(12) United States Patent
Liu et al.

(10) Patent No.: US 10,731,227 B2
(45) Date of Patent: Aug. 4, 2020

(54) COMPOSITIONS, KITS, AND METHODS TO DETECT HIV VIRUS

(71) Applicant: The Trustees of The University of Pennsylvania, Philadelphia, PA (US)

(72) Inventors: Changchun Liu, Bala Cynwyd, PA (US); Scott Sherrill-Mix, Philadelphia, PA (US); Haim H. Bau, Swarthmore, PA (US); Frederic D. Bushman, Rose Valley, PA (US); Karen E. Ocwieja, Philadelphia, PA (US); Jinzhao Song, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 164 days.

(21) Appl. No.: 15/534,835

(22) PCT Filed: Dec. 11, 2015

(86) PCT No.: PCT/US2015/065312
§ 371 (c)(1),
(2) Date: Jun. 9, 2017

(87) PCT Pub. No.: WO2017/099801
PCT Pub. Date: Jun. 15, 2017

(65) Prior Publication Data
US 2017/0362669 A1    Dec. 21, 2017

Related U.S. Application Data

(60) Provisional application No. 62/091,390, filed on Dec. 12, 2014.

(51) Int. Cl.
*C12Q 1/68*    (2018.01)
*C12Q 1/70*    (2006.01)
*C12Q 1/6853*  (2018.01)

(52) U.S. Cl.
CPC ......... *C12Q 1/703* (2013.01); *C12Q 1/6853* (2013.01); *C12Q 2600/158* (2013.01)

(58) Field of Classification Search
None
See application file for complete search history.

(56) References Cited

U.S. PATENT DOCUMENTS

| 6,503,705 | B1 | 1/2003 | Merigan et al. | |
| 8,900,807 | B2 * | 12/2014 | Owen | C12Q 1/703 435/5 |
| 2004/0034888 | A1 | 2/2004 | Liu et al. | |
| 2012/0088244 | A1 * | 4/2012 | Owen | C12Q 1/703 435/6.12 |

FOREIGN PATENT DOCUMENTS

| WO | 2008/121992 A2 | 10/2008 |
| WO | 2014/003583 A2 | 1/2014 |
| WO | 2015/118491 A1 | 8/2015 |

OTHER PUBLICATIONS

Brown et al. Biologic and genetic characterization of a panel of 60 human immunodeficiency virus type 1 isolates, representing clades A, B, C, D, CRF01_AE, and CRF02_AG, for the development and assessment of candidate vaccines. J Virol. May 2005; 79(10):6089-101. (Year: 2005).*
Curtis KA, Rudolph DL, Owen SM. Sequence-specific detection method for reverse transcription, loop-mediated isothermal amplification of HIV-1. Journal of medical virology. Jun. 2009; 81(6):966-72. (Year: 2009).*
Curtis KA, Niedzwiedz PL, Youngpairoj AS, Rudolph DL, Owen SM. Real-Time Detection of HIV-2 by Reverse Transcription-Loop-Mediated Isothermal Amplification. J Clin Microbiol. Jul. 2014; 52(7):2674-6. Epub Apr. 30, 2014. (Year: 2014).*
Notomi T, Okayama H, Masubuchi H, Yonekawa T, Watanabe K, Amino N, Hase T. Loop-mediated isothermal amplification of DNA. Nucleic Acids Res. Jun. 15, 2000; 28(12):E63 pp. 1-7. (Year: 2000).*
Zeng Y, Zhang X, Nie K, Ding X, Ring Bz, Xu L, Dai L, Li X, Ren W, Shi L, Ma X. Rapid quantitative detection of Human immunodeficiency virus type 1 by a reverse transcription-loop-mediated isothermal amplification assay. Gene. May 15, 2014; 541(2): 123-8. Epub Mar. 12, 2014. (Year: 2014).*
Zhao X, Chen X, Zhang Y, He X, Li W, Shi L, Chen X, Xu Z, Zhong N, Ji G, Yang L, Wang J. Development and evaluation of reverse-transcription loop-mediated isothermal amplification for rapid detection of human immunodeficiency virus type 1. Indian J Med Microbiol. Oct.-Dec. 2012; 30(4):391-6. (Year: 2012).*
Genbank Accession No. K03455—Human immunodeficiency virus type 1 (HXB2), complete genome; HIV1/HTLV-III/LAV reference genome (submitted Oct. 21, 2002, retrieved on Nov. 25, 2019 from http://www.ncbi.nlm.nih.gov/nuccore/K03455). (Year: 2002).*
Zhang et al., A Simple Statistical Parameter for Use in Evaluation and Validation of High Throughput Screening Assays, J Biomol Screen, 1999, 67-73, 4.

(Continued)

*Primary Examiner* — Gary Benzion
*Assistant Examiner* — Olayinka A Oyeyemi
(74) *Attorney, Agent, or Firm* — BakerHostetler

(57) ABSTRACT

Provided herein include compositions comprising a primer having the nucleic acid sequence of ACeIN-F3_c, a primer having the nucleic acid sequence of ACeIN-B3_a, a primer having the nucleic acid sequence of ACeIN-B3_b, a primer having the nucleic acid sequence of ACeIN-FIP_e, a primer having the nucleic acid sequence of ACeIN-FIP_f, a primer having the nucleic acid sequence of ACeIN-BIP (or ACeIN-BIP-song), a primer having the nucleic acid sequence of ACeIN-LF; and a primer having the nucleic acid sequence of ACeIN-LB. Also provided are methods of detecting human immunodeficiency virus (HIV) nucleic acids in a sample comprising performing reverse transcription-based loop mediated isothermal amplification (RT-LAMP) on a sample using the previously disclosed compositions.

15 Claims, 9 Drawing Sheets
Specification includes a Sequence Listing.

(56) References Cited

OTHER PUBLICATIONS

Sallis et al., Systematic review of the performance of HIV viral load technologies on plasma samples, PLoS One, 2014, e85869, 9.

Parrish et al., Phenotypic properties of transmitted founder HIV-1, Proc. Natl. Acad. Sci. US, Apr. 2013, 6626-6633, A 110.

Ocwieja et al., A Reverse Transcription Loop-Mediated Isothermal Amplification Assay Optimized to Detect Multiple HIV Subtypes. PLoS ONE Feb. 12, 2015, vol. 10, No. 2, pp. 1-11; abstract; p. 2, fourth-fifth paragraphs; p. 6. fourth paragraph; p. 9, second paragraph, sixth paragraph—p. 10, second paragraph; Tables S1, S2.

Notomi et al., Loop-mediated Isothermal amplification of DNA, Nucleic Acids, Jun. 2000, E63, 28.

Murray et al., Global, regional, and national incidence and mortality for HIV, tuberculosis, and malaria during 1990-2013: a systematic analysis for the Global Burden of Disease Study 2013, Lancet, Sep. 2014, 384(9947), 1005-1070.

Manak et al., Pilot studies for development of an HIV subtype panel for surveillance of global diversity, AIDS Res. Hum Retroviruses, Jun. 2012, 594-606, 28.

Liu et al., Membrane-based, sedimentation-assisted plasma separator for point-of-care applications., Anal Chem, 2013, 10463-10470, 85.

Liu et al., An isothermal amplification reactor with an integrated isolation membrane for point-of-care detection of Infectious diseases, Analyst, May 2011, 2069-2076, 136.

Kuiken et al., Viral genome analysis and knowledge management, Methods Mol. Biol., 2013, 253-261, 939.

Curtis et al., Sequence-specific detection method for reverse transcription, loop-mediated isothermal amplification of HIV-1, J. Med. Virol., 2009, 966-972, 81.

Curtis et al., Real-Time Detection of HIV-2 by Reverse Transcription-Loop-Mediated Isothermal Amplification, J. Clin. Microbial, Jul. 2014, 2674-2676, 52.

Curtis et al., Rapid detection of HIV-1 by reverse-transcription, loopmediated isothermal amplification (RT-LAMP), J. Virol Methods, 264-270, 151(2).

Curtis et al., Isothermal amplification using a chemical heating device for point-of-care detection of HIV-1, PLo-S One 2012, e31432, 7(2).

Buonaguro et al., Human immunodeficiency virus type 1 subtype distribution in the worldwide epidemic: pathogenetic and therapeutic implications, J. Virol, Oct. 2007, 10209-10219, 81.

Abimiku et al., Subgroup G HIV type 1 isolates from Nigeria, AIDS Res Hum Retroviruses, Nov. 1984, 1581-1583, 10.

\* cited by examiner

Figure 2
A
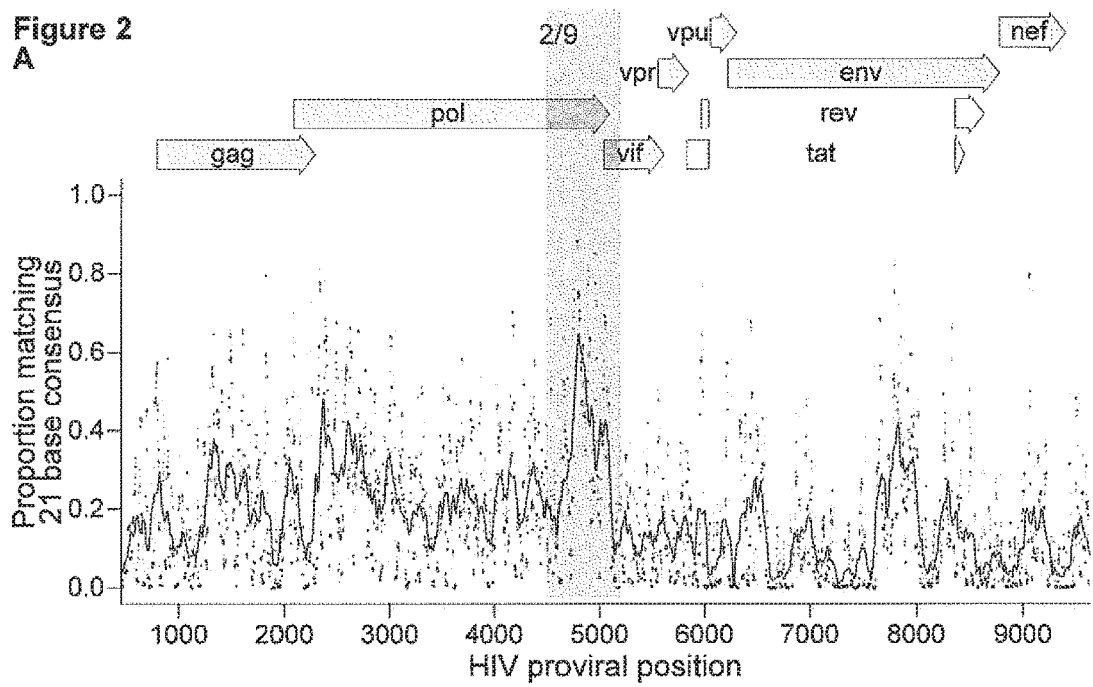
B
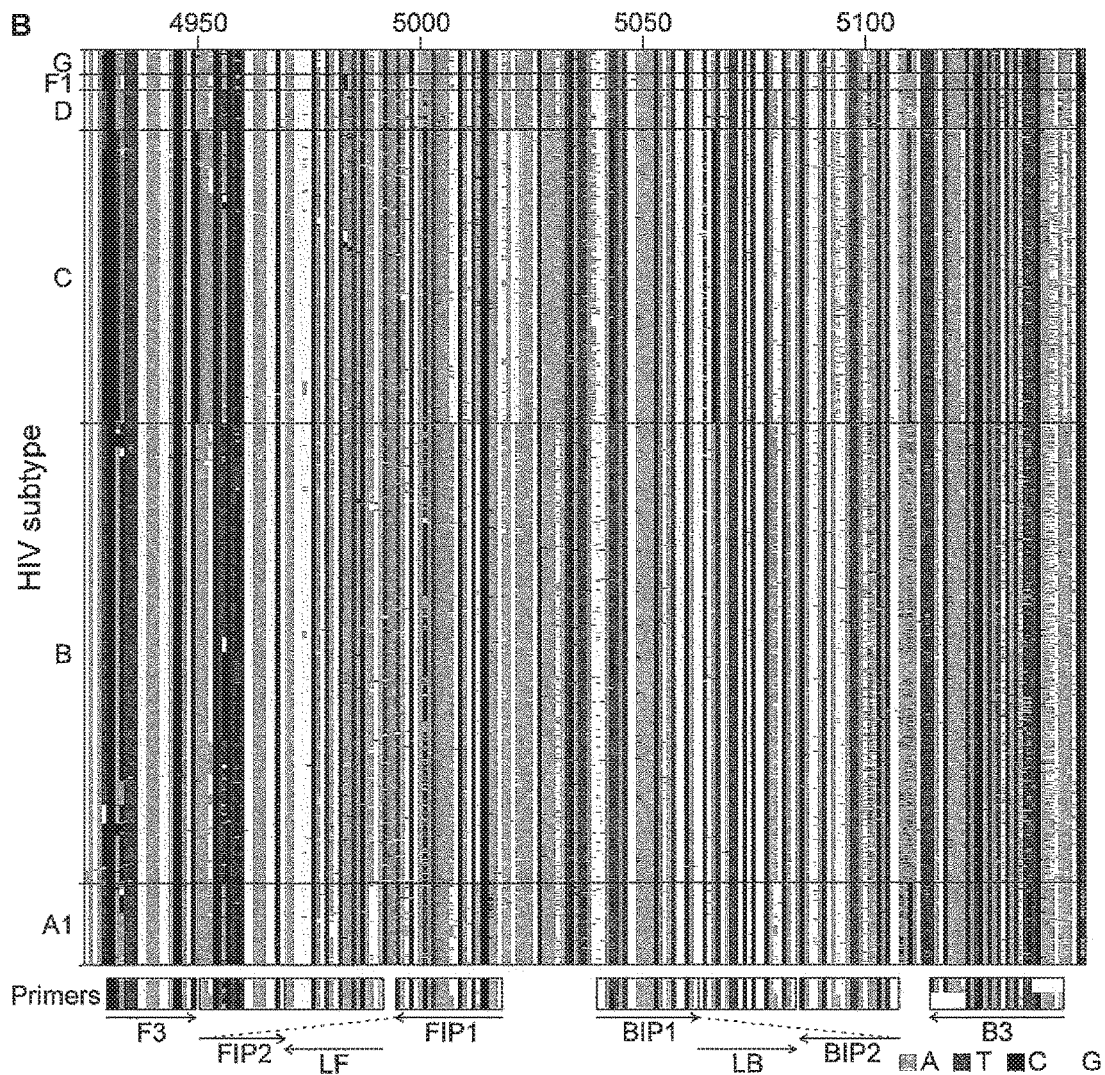

(A)

(B)

COMPOSITIONS, KITS, AND METHODS TO DETECT HIV VIRUS

CROSS-REFERENCE TO RELATED APPLICATIONS

This application is the National Stage Application of International Patent Application No. PCT/US2015/065312 filed Dec. 11, 2015, which claims the benefit of U.S. patent application Ser. No. 62/091,390, filed Dec. 12, 2014, the entire contents of which are incorporated by reference herein in their entirety.

GOVERNMENT RIGHTS

This invention was made with government support under grant number AI104418 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 25, 2017, is named 103241_000474_SL .txt and is 17,721 bytes in size.

TECHNICAL FIELD

The present inventions relate generally to compositions, kits, and methods for detecting HIV virus in a sample.

BACKGROUND

Despite the introduction of efficient antiretroviral therapy, HIV infection and AIDS continue to cause a world-wide health crisis. Further, there is a lack of quantitative viral load assays in the developing world. Thus, there is a need in the art for rapid and quantitative assays that can be used at the point of care with minimal infrastructure.

SUMMARY

In one aspect, the present disclosure provides compositions comprising: a primer having the nucleic acid sequence of ACeIN-F3_c, a primer having the nucleic acid sequence of ACeIN-B3_a, a primer having the nucleic acid sequence of ACeIN-B3_b, a primer having the nucleic acid sequence of ACeIN-FIP_e, a primer having the nucleic acid sequence of ACeIN-FIP_f, a primer having the nucleic acid sequence of ACeIN-BIP, a primer having the nucleic acid sequence of ACeIN-LF; and a primer having the nucleic acid sequence of ACeIN-LB. In another aspect, the present disclosure provides compositions comprising: a primer having the nucleic acid sequence of ACeIN-F3_c, a primer having the nucleic acid sequence of ACeIN-B3a, a primer having the nucleic acid sequence of ACeIN-B3b, a primer having the nucleic acid sequence of ACeIN-FIPe, a primer having the nucleic acid sequence of ACeIN-FIPf, a primer having the nucleic acid sequence of ACeIN-BIP-song, a primer having the nucleic acid sequence of ACeIN-LF; and a primer having the nucleic acid sequence of ACeIN-LB. Also provided are methods of detecting human immunodeficiency virus (HIV) nucleic acids in a sample comprising performing reverse transcription-based loop mediated isothermal amplification (RT-LAMP) on a sample using the previously disclosed compositions.

In another aspect, the present disclosure also provides methods of detecting human immunodeficiency virus (HIV) nucleic acids in a sample comprising contacting a reaction mixture comprising a reverse transcription-based loop mediated isothermal amplification assay of the previously disclosed composition, magnesium, dNTPs, a reaction buffer, a DNA polymerase and a sample to be tested for presence of HIV nucleic acids and incubating the reaction mixture under DNA polymerase reactions conditions so as to produce a reaction product comprising amplified HIV nucleic acids and detecting a reaction product.

Other aspects of the present disclosure include methods of detecting human immunodeficiency virus (HIV) in a patient comprising obtaining a sample from said patient and performing reverse transcription-based loop mediated isothermal amplification (RT-LAMP) on the sample using the previously disclosed compositions.

In another aspect, the present disclosure provides methods of detecting human immunodeficiency virus (HIV) in a patient comprising obtaining a sample from said patient and contacting a reaction mixture comprising a reverse transcription-based loop mediated isothermal amplification assay composition of claim 1 or claim 2, magnesium, dNTPs, a reaction buffer, a DNA polymerase and the sample to be tested for presence of HIV nucleic acids, incubating the reaction mixture under DNA polymerase reactions conditions to produce a reaction product comprising amplified HIV nucleic acids, and detecting a reaction product.

A further aspect of the present disclosure includes methods of monitoring a response to a medication in a subject in need thereof, comprising obtaining a first sample from the subject at a first time point, obtaining a second sample from the subject a second time point following administration of a medication to the subject, determining the amount of human immunodeficiency virus (HIV) in the first and second samples, the determining comprising, performing reverse transcription-based loop mediated isothermal amplification (RT-LAMP) on a sample containing HIV using the primers of claim 1 or claim 2, and comparing the amount of HIV in the first and second samples, wherein a decrease in the amount of HIV from the first sample relative to the second sample indicates treatment of HIV infection.

In another aspect, the present disclosure provides kits comprising a primer having the nucleic acid sequence of ACeIN-F3_c, a primer having the nucleic acid sequence of ACeIN-B3_a, a primer having the nucleic acid sequence of ACeIN-B3_b, a primer having the nucleic acid sequence of ACeIN-FIP_e, a primer having the nucleic acid sequence of ACeIN-FIP_f, a primer having the nucleic acid sequence of ACeIN-BIP, a primer having the nucleic acid sequence of ACeIN-LF, a primer having the nucleic acid sequence of ACeIN-LB, and packaging for said primers. In another aspect, the present disclosure provides kits comprising a primer having the nucleic acid sequence of ACeIN-F3_c, a primer having the nucleic acid sequence of ACeIN-B3a, a primer having the nucleic acid sequence of ACeIN-B3b, a primer having the nucleic acid sequence of ACeIN-FIPe, a primer having the nucleic acid sequence of ACeIN-FIPf, a primer having the nucleic acid sequence of ACeIN-BIP-song, a primer having the nucleic acid sequence of ACeIN-LF, a primer having the nucleic acid sequence of ACeIN-LB, and packaging for said primers.

BRIEF DESCRIPTION OF THE DRAWINGS

FIG. 2 shows bioinformatic analysis to design subtype-agnostic RT-LAMP primers. Part (A) shows conservation of sequence in HIV. HIV genomes (n=1340) from the Los Alamos National Laboratory collection (file HIV1_ALL_2012_genome_DNA.fasta; http://www.hiv.lan-1.gov/content/sequence/NEWALIGN/align.html#web) were aligned and conservation calculated. The x-axis shows the coordinate on the HIV genome, the y-axis shows the proportion matching the consensus in each 21 base segment of the genome (points). The black line shows a 101 base moving average over these proportions. The vertical shading shows the region targeted for LAMP primer design that was used as input into the EIKEN primer design tool. Numbering is relative to the $HIV_{89.6}$ sequence. Part (B) shows aligned genomes, showing the locations of the ACeIN26 primers. Sequences in the shaded region in A are shown, with DNA bases color-coded as shown at the lower right. Each row indicates an HIV sequence and each column a base in that sequence. Horizontal lines separate the HIV subtypes (labeled at right). Arrows indicate the strand targeted by each primer. Primers targeting the negative strand of the virus are shown as reverse compliments for ease of viewing.

DETAILED DESCRIPTION OF ILLUSTRATIVE EMBODIMENTS

Figure 1:
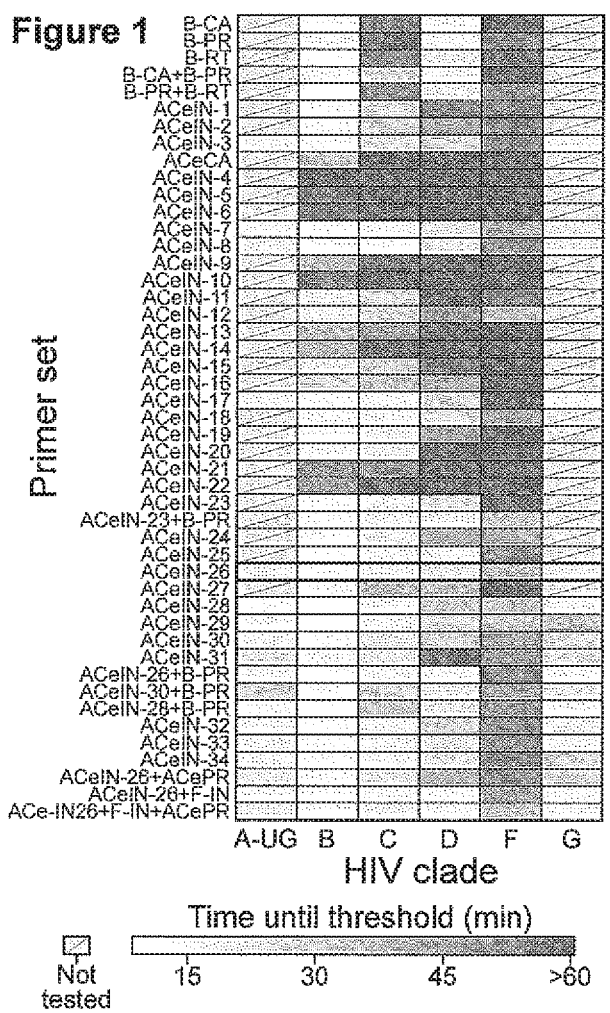
FIG. 1 shows a summary of amplification results for all the RT-LAMP primer sets tested in this study. The data is shown as a heat map, with more intense coloring indicating shorter amplification times (key at bottom). Primer sets tested are named along the left of the figure. Primer sequences, and their organization into LAMP primer sets, are cataloged in tables S1 and S2. The raw data and averaged data are collected in tables S3 and S4. ACeIN-26 primer set (highlighted) had one of the best performances across the subtypes and a relatively simple primer design.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

Despite the introduction of efficient antiretroviral therapy, HIV infection and AIDS continue to cause a world-wide health crisis. Methods for detecting HIV infection have developed with time. But quantitative viral load assays are not always available with on actionable time scales in much of the developing world, motivating the development of new rapid and quantitative assays that can be used at the point of care with minimal infrastructure.

One detection method involves reverse transcription-based loop mediated isothermal amplification (RT-LAMP). In this method, a DNA copy of the viral RNA is generated by reverse transcriptase, then isothermal amplification is carried out to increase the amount of total DNA.

Primer binding sites are chosen so that a series of strand displacement steps allow continuous synthesis of DNA without requiring thermocycling. Reaction products can be detected by adding a dye to reaction mixtures that fluoresces only when bound to DNA, allowing quantification of product formation by measurement of fluorescence intensity.

RT-LAMP assays for HIV-1 have been reported previously to show high sensitivity and specificity for subtype B, the most common HIV strain in the developed world. Assays have also been developed for HIV-2. However, a complication arises in using available RT-LAMP assays due to the variation of HIV genomic sequences among the HIV subtypes, so that an RT-LAMP assay optimized on one viral subtype may not detect viral RNA of another subtype. Tests presented below show that available RT-LAMP assays are efficient for detecting subtype B, for which they were designed, but often performed poorly on other subtypes, some of which are abundant world-wide.

In one aspect, the present disclosure provides development of an RT-LAMP assay capable of detecting HIV-1 subtypes A, B, C, D, and G. First, bioinformatic analysis was carried out to identify regions conserved in all the HIV subtypes. 44 different combinations of RT-LAMP primers targeting this region were tested in over 700 individual assays, allowing identification of primer sets (ACeIN-26 and ACeIN-35) that were optimal for detecting the subtypes tested. Optimized RT-LAMP assay may be useful for quantifying HIV RNA copy numbers in point-of-care applications in the developing world, where multiple different subtypes may be encountered.

Example 1. Testing Published RT-LAMP Primer Sets Against Multiple HIV Subtypes Performance of existing RT-LAMP assays on RNA samples from multiple HIV subtypes was assessed. Viral stocks from HIV subtypes A, B, C, D, F, and G, were obtained, and the numbers of virions per ml were quantified and RNA was extracted. RNAs were mixed with RT-LAMP reagents which included the six required RT-LAMP primers, designated F3, B3, FIP, BIP, LF and LB. Reactions also contained the intercalating fluorescent EvaGreen™ dye, which yields a fluorescent signal upon DNA binding. DNA synthesis was quantified as the increase in fluorescence over time, which yielded a typical curve describing exponential growth with saturation (examples are presented elsewhere herein). Results are expressed as threshold times (Tt) for achieving 10% amplification with 5000 HIV RNA template copies.

In initial tests, published primer sets targeting HIV CA, PR, and RT were assayed (named B-CA, B-PR and B-RT). In the following, results with each primer set tested are shown in FIG. 1 in heat map format. Primers and their grouping into sets are summarized in Tables 1 and 2, average assay results are in Table 3, and raw assay data is in Table 4.

Table 1 shows the primer sequences used.

TABLE 1

| Primer | Sources | Sequence (5' to 3') | SEQ ID NO: |
|---|---|---|---|
| B-CA-F3 | [1] | ATTATCAGAAGGAGCCACC | 1 |
| F-CA-B3 | [1] | CATCCTATTTGTTCCTGAAGG | 2 |
| B-CA-FIP | [1] | CAGCTTCCTCATTGATGGTTTCTTTTTAACACCATGCTAAACACAGT | 3 |
| B-CA-BIP | [1] | TGTTGCACCAGGCCAGATAATTTTGTACTGGTAGTTCCTGCTATG | 4 |
| B-CA-LF | [1] | TTTAACATTTGCATGGCTGCTTGAT | 5 |
| B-CA-LB | [1] | GAGATCCAAGGGGAAGTGA | 6 |
| ACeCA-F3 | This work | CCCTTTAGAGACTATGTAGACC | 7 |
| ACeCA-B3 | This work | TCCTACTCCCTGACATGC | 8 |
| ACeCA-FIP | This work | CAACAAGGTTTCTGTCATCCAATTTGGTTCTATAAAACTCTAAGAGCC | 9 |
| ACeCA-BIP | This work | GTCCAAAATGCGAACCCAGATGTCATCATTTCTTCTAGTGTAG | 10 |
| ACeCA-LF | This work | TACCTCCTGTGAAGCTTGCTC | 11 |
| ACeCA-LB | This work | TTTAAAAGCATTGGGACCAGCGG | 12 |
| B-PR-F3 | [1] | AAAGATAGGGGGCAACT | 13 |
| B-PR-B3 | [1] | GTTGACAGGTGTAGGTCCTA | 14 |
| B-PR-FIP | [1] | GGTTTCCATCTTCCTGGCAAATTTTTTCTCTATTAGATACAGGAGCAGA | 15 |
| B-PR-BIP | [1] | TGATAGGGGAATTGGAGGTTTTTTCCTATAGCTTTATGTCCACAGA | 16 |
| B-PR-LF | [1] | TTCCTATAGCTTTATGTCCACAGA | 17 |
| B-PR-LB | [1] | TATCAAAGTAAGACAGTA | 18 |
| A-PR-F3 | This work | AARARTAGGRGGACAGCT | 19 |
| C-PR-F3 | This work | AAAAGTAGGGGGCCAGRT | 20 |
| F-PF-F3 | This work | AAAAGTAGGGGGACAGCT | 21 |
| AC-PR-F3b | This work | CACTCTTTGGCAACGACC | 22 |
| AC-PR-B3 | This work | ATGTTGACAGGTGTAGGYCC | 23 |
| AC-PR-FIP | This work | GGTTTCCATCTTCCTGGCAAATTTTTTCTCTATTAGAYACAGGAGCAGA | 24 |

TABLE 1-continued

| Primer | Sources | Sequence (5' to 3') | SEQ ID NO: |
|---|---|---|---|
| AC-PR-BIPa | This work | TGATAGGRGGAATTGGAGGTTTTTTCCTATAGCYTTWTKTCCACARA | 25 |
| AC-PR-BIPb | This work | TGATAGGRGGAATTGGAGGTTTTTTGCYTTWTKTCCACARATTTCTA | 26 |
| AC-PR-LF | This work | TATDTCTTCTAATACTGTATCA | 27 |
| AC-PR-LB | This work | ATCAAAGTAAGACARTAT | 28 |
| B-RT-F3 | [2] | AGTTCCCTTAGATAAAGACTT | 29 |
| B-RT-B3 | [2] | CCTACATACAAATCATCCATGT | 30 |
| B-RT-FIP | [2] | GTGGAAGCACATTGTACTGATATCTTTTTGGAAGTATACTGCATTTACCAT | 31 |
| B-RT-BIP | [2] | GGAAAGGATCACCAGCAATATTCCTCTGGATTTTGTTTTCTAAAAGGC | 32 |
| B-RT-LF | [2] | GGTGTCTCATTGTTTATACTA | 33 |
| B-RT-LB | [2] | GCATGACAAAAATCTTAGA | 34 |
| ACeIN-F3 | This work | TATTTGGAAAGGACCAGC | 35 |
| ACeIN-F3_b | This work | CGGGTTTATTACAGRGACAGCA | 36 |
| ACeIN-F3_c | This work | CCTATTTGGAAAGGACCAGC | 37 |
| ACeIN-F3_cL | This work | CCTATTTGGAAAGG + ACCAGC | 38 |
| ACeIN-B3a | This work | TCTTTGAAAYATACATATGRTG | 39 |
| ACeIN-B3a_L | This work | TCTTT + GAAAYATACATATGRTG | 40 |
| ACeIN-B3b | This work | AACATACATATGRTGYTTTACTA | 41 |
| ACeIN-B3bL | This work | AACA + TACATAT + GRTGYTTTACTA | 42 |
| ACeIN-FIPa | This work | CTTGGTACTACCTTTATGTCACTAAAGCTCCTCTGGAAAGGTG | 43 |
| ACeIN-FIPa_T | This work | CTTGGTACTACCTTTATGTCACTATTTTAAGCTCCTCTGGAAAGGTG | 44 |
| ACeIN-FIPb | This work | CTTGGCACTACTTTATGTCACTAAAGCTCCTCTGGAAAGGTG | 45 |
| ACeIN-FIPb_T | This work | CTTGGCACTACTTTATGTCACTATTTTAAGCTCCTCTGGAAAGGTG | 46 |
| ACeIN-FIPe | This work | CTTGGTACTACYTTTATGTCACTAAARCTACTCTGGAAAGGTG | 47 |
| ACeIN-FIPe_T | This work | CTTGGTACTACYTTTATGTCACTATTTTAARCTACTCTGGAAAGGTG | 48 |
| ACeIN-FIPe_L | This work | CTTGGTACTACYTTTA + TGT + CACTAAARC + TACTCT + GGAAAGGTG | 49 |
| ACeIN-FIPf | This work | CTTGGCACTACYTTTATGTCACTAAARCTYCTCTGGAAAGGTG | 50 |
| ACeIN-FIPf_T | This work | CTTGGCACTACYTTTATGTCACTATTTTAARCTYCTCTGGAAAGGTG | 51 |
| ACeIN-FIPf_L | This work | CTTGGCACTACYTTTATGTCACTAAARCTYCTCT + GGAAAGGTG | 52 |
| ACeIN-FIPg | This work | CTYCTTGGTACTACCTTTATGTCATACTCTGGAAAGGTGAAGG | 53 |
| ACeIN-FIPg_T | This work | CTYCTTGGTACTACCTTTATGTCATTTTTACTCTGGAAAGGTG | 54 |

TABLE 1-continued

| Primer | Sources | Sequence (5' to 3') | SEQ ID NO: |
|---|---|---|---|
| ACeIN-FIPh | This work | CTTCTTGGCACTACTTTTATGTCATYCTC TGGAAAGGTGAAGG | 55 |
| ACeIN-FIPh_T | This work | CTTCTTGGCACTACTTTTATGTCATTTTT YCTCTGGAAAGGTG | 56 |
| ACeIN-FIPi | This work | GGYACTACYTTTATGTCACTATTRTCCCT ATTTGGAAAGGACCAGC | 57 |
| ACeIN-FIPi_T | This work | GGYACTACYTTTATGTCACTATTRTCTTT TCCTATTTGGAAAGGACCAGC | 58 |
| ACeIN-FIPj | This work | CTTGGTACTACCTTTATGTCACTAAAACT ACTCTGGAAAGGTG | 59 |
| ACeIN-FIPj_T | This work | CTTGGTACTACCTTTATGTCACTATTTTA AACTACTCTGGAAAGGTG | 60 |
| ACeIN-FIPk | This work | CTTGGCACTACTTTTATGTCACTAAAGCT YCTCTGGAAAGGTG | 61 |
| ACeIN-FIPk_T | This work | CTTGGCACTACTTTTATGTCACTATTTTA AGCTYCTCTGGAAAGGTG | 62 |
| ACeIN-BIP | This work | GGAYTATGGAAAACAGATGGCAGCCAT GTTCTAATCYTCATCCTG | 63 |
| ACeIN-BIP-song | This work | GGAYTATGGAAAACAGATGGCAGCCAT GYYCTRATCYTCATCCTG | 64 |
| ACeIN-BIP_T | This work | GGAYTATGGAAAACAGATGGCAGTTTTC CATGTTCTAATCYTCATCCTG | 65 |
| ACeIN-BIP_LT | This work | GGAYTATGGAAAA + CAGATGGCAGTTTT CCATGTTCTAA + TCYTCATCCTG | 66 |
| ACeIN-LF | This work | TCTTGTATTACTACTGCCCCTT | 67 |
| ACeIN-LF_b | This work | CTATTGTCTTGTATTACTACTGC | 68 |
| ACeIN-LF_c | This work | CTACTGCCCCTTCACCTTTCCA | 69 |
| ACeIN-LB | This work | GTGATGATTGTGTGGCARGTAG | 70 |
| F-IN-F3 | This work | AGTTTGGAAAGGACCAGC | 71 |
| F-IN-B3a | This work | TCTTTGAAACATGCATATGGTA | 72 |
| F-IN-B3b | This work | AACATACATATGGTATTTTACTA | 73 |
| F-IN-FIP | This work | CTTGGTACTACCTTTATTTCACTAAAGCT ACTCTGGAAAGGTG | 74 |
| F-IN-BIP | This work | GGATTATGGAAAACAGATGGCAGCCATG TGTTAATCCTCATCCTG | 75 |
| F-IN-LF | This work | CTTGTATGACTACTGCCCCTT | 76 |
| F-IN-LB | This work | GTGATGATTGTGTGGCAGGTAG | 77 |

Note:
"+" in sequences indicates the following base is an LNA base.

REFERENCES

1. Curtis K A, Rudolph D L, Owen S M, Rapid detection of HIV-1 by reverse-transcription, loop-mediated isothermal amplification (RT-LAMP), J Virol Methods. 2008, 151(2): 264-70.
2. Curtis K A, Rudolph D L, Nejad I, Singleton J, Beddoe A, Weigl B, LaBarre P, Owen S M, Isothermal amplification using a chemical heating device for point-of-care detection of HIV-1. PLoS One. 2012; 7(2):e31432.

Assays (FIG. 1, top) with the B-CA, B-PR and B-RT primer sets detected subtypes B and D at 5000 RNA copies with threshold times less than 20 min. However, assays with all three detected subtypes C and F with threshold times >50 min, and B-PR did not detect subtype C at all. In an effort to improve the breadth of detection, B-PR primers were mixed, which detected clade F (albeit with limited efficiency) with the B-CA and B-RT primers (FIG. 1 and Table 3 and 4). In neither case did this provide coverage of all four clades tested. Primer sets targeting additional regions of the HIV genome were thus sought.

Example 2-Primer Design Strategy

To design primers that detected multiple HIV subtypes efficiently, first HIV genomes (downloaded from the LANL site) were aligned to identify the most conserved regions, revealing that a segment of the pol gene encoding IN was particularly conserved (FIG. 2A). A total of six primers are required for each RT-LAMP assay. The EIKEN™ primer design tool was used to identify an initial primer set targeting this region. In further analysis, positions in the alignments were identified within primer landing sites that commonly contained multiple different bases. Primer mixtures were formulated containing each of these commonly occurring bases (Table 1 and Table 2). An extensive series of variants targeting the IN coding region was tested empirically in assays containing RNAs from multiple subtypes (5000 RNA copies per reaction, over 700 total assays; Tables 3 and 4). Primers were further modified based on measured performance.

Table 2 shows the HIV RT-LAMP primer sets studied.

TABLE 2

| Primer set | Primers set name | Sources | Primers* |
|---|---|---|---|
| 1 | B-CA | [1] | B-CA-F3, B-CA-B3, B-CA-FIP, B-CA-BIP, B-CA-LF, B-CA-LB |
| 2 | B-PR | [1] | B-PR-F3, B-PR-B3, B-PR-FIP, B-PR-BIP, B-PR-LF, B-PR-LB |
| 3 | B-RT | [2] | B-RT-F3, B-RT-B3, B-RT-FIP, B-RT-BIP, B-RT-LF, B-RT-LB |
| 4 | B-CA + B-PR | This work | B-CA-F3, B-CA-B3, B-CA-FIP, B-CA-BIP, B-CA-LF, B-CA-LB, B-PR-F3, B-PR-B3, B-PR-FIP, B-PR-BIP, B-PR-LF, B-PR-LB |
| 5 | B-PR + B-RT | This work | B-PR-F3, B-PR-B3, B-PR-FIP, B-PR-BIP, B-PR-LF, B-PR-LB, B-RT-F3, B-RT-B3, B-RT-FIP, B-RT-BIP, B-RT-LF, B-RT-LB |
| 6 | ACeIN-1 | This work | ACeIN-F3, ACeIN-B3a, ACeIN-FIPa, ACeIN-FIPb, ACeIN-BIP, ACeIN-LF, ACeIN-LB |
| 7 | ACeIN-2 | This work | ACeIN-F3, ACeIN-B3b, ACeIN-FIPa, ACeIN-FIPb, ACeIN-BIP, ACeIN-LF, ACeIN-LB |
| 8 | ACeIN-3 | This work | ACeIN-F3, ACeIN-B3a, ACeIN-B3b, ACeIN-FIPa, ACeIN-FIPb, ACeIN-BIP, ACeIN-LF,, ACeIN-LB |
| 9 | ACeCA | This work | ACeCA-F3, ACeCA-B3, ACeCA-FIP, ACeCA-BIP, ACeCA-LF, ACeCA-LB |
| 10 | ACeIN-4 | This work | ACeIN-F3, ACeIN-B3a, ACeIN-B3b, ACeIN-FIPa, ACeIN-FIPb, ACeIN-BIP_T, ACeIN-LF, ACeIN-LB |
| 11 | ACeIN-5 | This work | ACeIN-F3, ACeIN-B3a, ACeIN-B3b, ACeIN-FIPa_T, ACeIN-FIPb_T, ACeIN-BIP, ACeIN-LF, ACeIN-LB |
| 12 | ACeIN-6 | This work | ACeIN-F3, ACeIN-B3a, ACeIN-B3b, ACeIN-FIPa_T, ACeIN-FIPb_T, ACeIN-BIP_T, ACeIN-LF, ACeIN-LB |
| 13 | ACeIN-7 | This work | ACeIN-F3, ACeIN-B3a, ACeIN-B3b, ACeIN-FIPe, ACeIN-FIPf, ACeIN-BIP, ACeIN-LF, ACeIN-LB |
| 14 | ACeIN-8 | This work | ACeIN-F3, ACeIN-B3a, ACeIN-B3b, ACeIN-FIPe, ACeIN-FIPf, ACeIN-BIP_T, ACeIN-LF, ACeIN-LB |
| 15 | ACeIN-9 | This work | ACeIN-F3, ACeIN-B3a, ACeIN-B3b, ACeIN-FIPe_T, ACeIN-FIPf_T, ACeIN-BIP, ACeIN-LF, ACeIN-LB |
| 16 | ACeIN-10 | This work | ACeIN-F3, ACeIN-B3a, ACeIN-B3b, ACeIN-FIPe_T, ACeIN-FIPf_T, ACeIN-BIP_T, ACeIN-LF, ACeIN-LB |
| 17 | ACeIN-11 | This work | ACeIN-F3, ACeIN-B3a, ACeIN-B3b, ACeIN-FIPg, ACeIN-FIPh, ACeIN-BIP, ACeIN-LF_b, ACeIN-LB |
| 18 | ACeIN-12 | This work | ACeIN-F3, ACeIN-B3a, ACeIN-B3b, ACeIN-FIPg, ACeIN-FIPh, ACeIN-BIP_T, ACeIN-LF_b, ACeIN-LB |
| 19 | ACeIN-13 | This work | ACeIN-F3, ACeIN-B3a, ACeIN-B3b, ACeIN-FIPg_T, ACeIN-FIPh_T, ACeIN-BIP, ACeIN-LF_b, ACeIN-LB |
| 20 | ACeIN-14 | This work | ACeIN-F3, ACeIN-B3a, ACeIN-B3b, ACeIN-FIPg_T, ACeIN-FIPh_T, ACeIN-BIP_T, ACeIN-LF_b, ACeIN-LB |
| 21 | ACeIN-15 | This work | ACeIN-F3_b, ACeIN-B3a, ACeIN-B3b, ACeIN-FIPi, ACeIN-BIP, ACeIN-LF_c, ACeIN-LB |
| 22 | ACeIN-16 | This work | ACeIN-F3_b, ACeIN-B3a, ACeIN-B3b, ACeIN-FIPi, ACeIN-BIP_T, ACeIN-LF_c, ACeIN-LB |
| 23 | ACeIN-17 | This work | ACeIN-F3, ACeIN-B3a, ACeIN-B3b, ACeIN-FIPj, ACeIN-FIPk, ACeIN-BIP, ACeIN-LF, ACeIN-LB |
| 24 | ACeIN-18 | This work | ACeIN-F3, ACeIN-B3a, ACeIN-B3b, ACeIN-FIPj, ACeIN-FIPk, ACeIN-BIP_T, ACeIN-LF, ACeIN-LB |
| 25 | ACeIN-19 | This work | ACeIN-F3_b, ACeIN-B3a, ACeIN-B3b, ACeIN-FIPi_T, ACeIN-BIP, ACeIN-LF_c, ACeIN-LB |
| 26 | ACeIN-20 | This work | ACeIN-F3_b, ACeIN-B3a, ACeIN-B3b, ACeIN-FIPi_T, ACeIN-BIP_T, ACeIN-LF_c, ACeIN-LB |
| 27 | ACeIN-21 | This work | ACeIN-F3, ACeIN-B3a, ACeIN-B3b, ACeIN-FIPj_T, ACeIN-FIPk_T, ACeIN-BIP, ACeIN-LF, ACeIN-LB |
| 28 | ACeIN-22 | This work | ACeIN-F3, ACeIN-B3a, ACeIN-B3b, ACeIN-FIPj_T, ACeIN-FIPk_T, ACeIN-BIP_T, ACeIN-LF, ACeIN-LB |
| 29 | ACeIN-23 | This work | ACeIN-F3, ACeIN-F3_c, ACeIN-B3a, ACeIN-B3b, ACeIN-FIPa, ACeIN-FIPb, ACeIN-FIPe, ACeIN-FIPf, ACeIN-FIPj, ACeIN-FIPk, ACeIN-BIP, ACeIN-BIP_T, ACeIN-LF, ACeIN-LB |
| 30 | ACeIN-23 + B-PR | This work | ACeIN-F3, ACeIN-F3_c, ACeIN-B3a, ACeIN-B3b, ACeIN-FIPa, ACeIN-FIPb, ACeIN-FIPe, ACeIN-FIPf, ACeIN-FIPj, ACeIN-FIPk, ACeIN-BIP, ACeIN-BIP_T, ACeIN-LF, ACeIN-LB, B-PR-F3, B-PR-B3, B-PR-FIP, B-PR-BIP, B-PR-LF, B-PR-LB |
| 31 | ACeIN-24 | This work | ACeIN-F3_cL, ACeIN-B3a_L, ACeIN-B3b_L, ACeIN-FIPe, ACeIN-FIPf, ACeIN-BIP_LT, ACeIN-LF, ACeIN-LB |
| 32 | ACeIN-25 | This work | ACeIN-F3_c, ACeIN-B3a, ACeIN-B3b, ACeIN-FIPa, ACeIN-FIPb, ACeIN-BIP, ACeIN-LF, ACeIN-LB |

TABLE 2-continued

| Primer set | Primers set name | Sources | Primers* |
|---|---|---|---|
| 33 | ACeIN-26 | This work | ACeIN-F3_c, ACeIN-B3a, ACeIN-B3b, ACeIN-FIPe, ACeIN-FIPf, ACeIN-BIP, ACeIN-LF, ACeIN-LB |
| 34 | ACeIN-27 | This work | ACeIN-F3_c, ACeIN-B3a, ACeIN-B3b, ACeIN-FIPe, ACeIN-FIPf, ACeIN-BIP_T, ACeIN-LF, ACeIN-LB |
| 35 | ACeIN-28 | This work | ACeIN-F3_c, ACeIN-B3a, ACeIN-B3b, ACeIN-FIPj, ACeIN-FIPk, ACeIN-BIP, ACeIN-LF, ACeIN-LB |
| 36 | ACeIN-29 | This work | ACeIN-F3_c, ACeIN-B3a, ACeIN-B3b, ACeIN-FIPj, ACeIN-FIPk, ACeIN-BIP_T, ACeIN-LF, ACeIN-LB |
| 37 | ACeIN-30 | This work | ACeIN-F3_c, ACeIN-B3a, ACeIN-B3b, ACeIN-FIPe_L, ACeIN-FIPf_L, ACeIN-BIP, ACeIN-LF, ACeIN-LB |
| 38 | ACeIN-31 | This work | ACeIN-F3_c, ACeIN-B3a, ACeIN-B3b, ACeIN-FIPe_L, ACeIN-FIPf_L, ACeIN-BIP_LT, ACeIN-LF, ACeIN-LB |
| 39 | ACeIN-26 + B-PR | This work | ACeIN-F3_c, ACeIN-B3a, ACeIN-B3b, ACeIN-FIPe, ACeIN-FIPf, ACeIN-BIP, ACeIN-LF, ACeIN-LB, B-PR-F3, B-PR-B3, B-PR-FIP, B-PR-BIP, B-PR-LF, B-PR-LB |
| 40 | ACeIN-30 + B-PR | This work | ACeIN-F3_c, ACeIN-B3a, ACeIN-B3b, ACeIN-FIPe_L, ACeIN-FIPf_Lm ACeIN-BIP, ACeIN-LF, ACeIN-LB, B-PR-F3, B-PR-B3, B-PR-FIP, B-PR-BIP, B-PR-LF, B-PR-LB |
| 41 | ACeIN-28 + B-PR | This work | ACeIN-F3_c, ACeIN-B3a, ACeIN-B3b, ACeIN-FIPj, ACeIN-FIPk, ACeIN-BIP, ACeIN-LF, ACeIN-LB, B-PR-F3, B-PR-B3, B-PR-FIP, B-PR-BIP, B-PR-LF, B-PR-LB |
| 42 | ACeIN-32 | This work | ACeIN-F3_cL, ACeIN-B3a, ACeIN-B3b, ACeIN-FIPe, ACeIN-FIPf ACeIN-BIP, ACeIN-LF, ACeIN-LB |
| 43 | ACeIN-33 | This work | ACeIN-F3_c, ACeIN-B3a_L, ACeIN-B3b_L, ACeIN-FIPe, ACeIN-FIPf, ACeIN-BIP, ACeIN-LF, ACeIN-LB |
| 44 | ACeIN-34 | This work | ACeIN-F3_cL, ACeIN-B3a_L, ACeIN-B3b_L, ACeIN-FIPe, ACeIN-FIPf, ACeIN-BIP, ACeIN-LF, ACeIN-LB |
| 45 | ACeIN-26 + ACePR | This work | ACeIN-F3_c, ACeIN-B3a, ACeIN-B3b, ACeIN-FIPe, ACeIN-FIPf, ACeIN-BIP, ACeIN-LF, ACeIN-LB, A-PR-F3, B-PR-F3, C-PR-F3, F-PR-F3, AC-PR-F3b, AC-PR-B3, AC-PR-FIP, AC-PR-BIPa, AC-PR-BIPb, AC-PR-LF, AC-PR-LB |
| 46 | ACeIN-26 + F-IN | This work | ACeIN-F3_c, ACeIN-B3a, ACeIN-B3b, ACeIN-FIPe, ACeIN-FIPf, ACeIN-BIP, ACeIN-LF, ACeIN-LB, F-IN-F3, F-IN-B3a, F-IN-B3b, F-IN-FIP, F-IN-BIP, F-IN-LF, F-IN-LB |
| 47 | Ace-IN26 + F-IN + ACePR | This work | ACeIN-F3_c, ACeIN-B3a, ACeIN-B3b, ACeIN-FIPe, ACeIN-FIPf, ACeIN-BIP, ACeIN-LF, ACeIN-LB, F-IN-F3, F-IN-B3a, F-IN-B3b, F-IN-FIP, F-IN-BIP, F-IN-LF, F-IN-LB, A-PR-F3, B-PR-F3, C-PR-F3, F-PR-F3, AC-PR-F3b, AC-PR-B3, AC-PR-FIP, AC-PR-BIPa, AC-PR-BIPb, AC-PR-LF, AC-PR-LB |
| 48 | ACeIN-35 | This work | ACeIN-F3_c, ACeIN-B3a, ACeIN-B3b, ACeIN-B3b, ACeIN-FIPe, ACeIN-FIPf, ACeIN-BIP-song, ACeIN-LF, ACeIN-LB |

Table 3 shows average threshold times. Reactions contained 5000 copies of HIV-1 RNA templates from the subtypes listed at the tops of the columns. The threshold time ($T_t$) is defined as the reaction time that elapses until the threshold signal increases 10% of maximum fluorescence intensity ($I_{max}$) above the baseline level.

TABLE 3

Table S3. Average threshold times (5000 copies).

| | | Clade | | | | | | |
|---|---|---|---|---|---|---|---|---|
| Primer set | Primers set name | A-UG $T_t$(min) | B $T_t$(min) | C $T_t$(min) | D $T_t$(min) | F $T_t$(min) | G $T_t$(min) | Average $T_t$(min) |
| 1 | B-CA | — | 12.5 | 54.77 | 13.3 | 59.34 | — | 34.98 |
| 2 | B-PR | — | 16.07 | 61 | 15.38 | 51.85 | — | 36.08 |
| 3 | B-RT | — | 8.82 | 52.88 | 19.86 | 56.48 | — | 34.51 |
| 4 | B-CA + B-PR | — | 13.16 | 24.15 | 14.14 | 61 | — | 28.11 |
| 5 | B-PR + B-RT | — | 8.46 | 50.36 | 18.17 | 48.91 | — | 31.47 |
| 6 | ACeIN-1 | — | 10.91 | 24.45 | 51.63 | 53.99 | — | 35.25 |
| 7 | ACeIN-2 | — | 10.16 | 26.86 | 40.61 | 52.34 | — | 32.49 |
| 8 | ACeIN-3 | 14.37 | 9.12 | 22.43 | 25.17 | 50.52 | 14.43 | 22.67 |
| 9 | ACeCA | — | 32.34 | 61 | 61 | 61 | — | 53.84 |
| 10 | ACeIN-4 | — | 61 | 61 | 61 | 61 | — | 61 |
| 11 | ACeIN-5 | — | 55 | 61 | 61 | 61 | — | 59.5 |
| 12 | ACeIN-6 | — | 53.12 | 61 | 61 | 61 | — | 59.03 |
| 13 | ACeIN-7 | 14.09 | 9.04 | 14 | 21.3 | 40.81 | 19.08 | 19.72 |
| 14 | ACeIN-8 | 16.66 | 9.86 | 11.89 | 21.19 | 48.82 | 17.39 | 20.97 |
| 15 | ACeIN-9 | — | 34.35 | 61 | 61 | 61 | — | 54.34 |
| 16 | ACeIN-10 | — | 53.87 | 61 | 61 | 61 | — | 59.22 |
| 17 | ACeIN-11 | — | 16.07 | 25.36 | 61 | 51.47 | — | 38.47 |
| 18 | ACeIN-12 | — | 15.94 | 24.72 | 46.73 | 33.02 | — | 30.1 |
| 19 | ACeIN-13 | — | 34.81 | 45.74 | 61 | 61 | — | 50.64 |

TABLE 3-continued

| | | | | | | | | |
|---|---|---|---|---|---|---|---|---|
| 20 | ACeIN-14 | — | 39.54 | 61 | 61 | 61 | — | 55.63 |
| 21 | ACeIN-15 | — | 19.54 | 29.3 | 56.99 | 61 | — | 41.71 |
| 22 | ACeIN-16 | — | 26.45 | 31.12 | 41.26 | 61 | — | 39.96 |
| 23 | ACeIN-17 | 15.31 | 9.41 | 13.71 | 27.49 | 61 | 13.47 | 23.4 |
| 24 | ACeIN-18 | — | 13.39 | 17 | 25.26 | 43.91 | — | 24.89 |
| 25 | ACeIN-19 | — | 13.08 | 17.29 | 42.85 | 61 | — | 33.55 |
| 26 | ACeIN-20 | — | 15.38 | 20.55 | 61 | 61 | — | 39.48 |
| 27 | ACeIN-21 | — | 47.2 | 52.82 | 61 | 61 | — | 55.51 |
| 28 | ACeIN-22 | — | 46.73 | 59.34 | 61 | 61 | — | 57.02 |
| 29 | ACeIN-23 | — | 10.82 | 16.13 | 24.46 | 61 | — | 28.1 |
| 30 | ACeIN-23 + B-P | — | 10.45 | 17.14 | 17.62 | 33.89 | — | 19.77 |
| 31 | ACeIN-24 | — | 12.21 | 19.89 | 41.88 | 41.74 | — | 28.93 |
| 32 | ACeIN-25 | — | 8.91 | 14.02 | 14.41 | 46.49 | — | 20.96 |
| 33 | ACeIN-26 | 15.95 | 9.88 | 14.46 | 20.79 | 34.69 | 18.89 | 19.11 |
| 34 | ACeIN-27 | — | 12.55 | 37.7 | 36.48 | 61 | — | 36.93 |
| 35 | ACeIN-28 | 10.69 | 9.4 | 15.99 | 33.39 | 34.83 | 16.57 | 20.15 |
| 36 | ACeIN-29 | 14.02 | 10.68 | 14.87 | 26.12 | 31.39 | 35.95 | 22.17 |
| 37 | ACeIN-30 | 16.69 | 11.33 | 20.64 | 29.01 | 43.2 | 24.25 | 24.19 |
| 38 | ACeIN-31 | 23.25 | 15.02 | 21.67 | 61 | 46.37 | 24.62 | 31.99 |
| 39 | ACeIN-26 + B-PR | 16.1 | 9.05 | 14.73 | 14.8 | 51.26 | 14.05 | 20 |
| 40 | ACeIN-30 + B-PR | 29.95 | 10.38 | 28.49 | 20.33 | 42.46 | 23.09 | 25.78 |
| 41 | ACeIN-28 + B-PR | 11.44 | 9.93 | 33.62 | 21.75 | 46.72 | 13.41 | 22.81 |
| 42 | ACeIN-32 | 16.16 | 10.39 | 15.98 | 29.17 | 51.34 | 17.71 | 23.46 |
| 43 | ACeIN-33 | 16.27 | 10.48 | 15.81 | 22.75 | 50.48 | 16.79 | 22.1 |
| 44 | ACeIN-34 | 15.9 | 10.22 | 14.35 | 22.63 | 51.99 | 27.15 | 23.71 |
| 45 | ACeIN-26 + AC | 21.66 | 12.16 | 23.47 | 39.13 | 50.33 | 26.09 | 28.81 |
| 46 | ACeIN-26 + F-IN | 14.51 | 12.35 | 15.06 | 13.54 | 43.39 | 15.61 | 19.08 |
| 47 | ACeIN-26 + F-IN + ACePR | 19.69 | 13.08 | 18.45 | 14.91 | 35.13 | 16.09 | 19.56 |

Table S3. Average threshold times.

| Primer set | Primers set name | A-UG $T_t$(min) | B $T_t$(min) | C $T_t$(min) | D $T_t$(min) | F $T_t$(min) | G $T_t$(min) | Average $T_t$(min) |
|---|---|---|---|---|---|---|---|---|
| 1 | B-CA | — | 12.5 | 54.77 | 13.3 | 59.34 | — | 34.98 |
| 2 | B-PR | — | 16.07 | 61 | 15.38 | 51.85 | — | 36.08 |
| 3 | B-RT | — | 8.82 | 52.88 | 19.86 | 56.48 | — | 34.51 |
| 4 | B-CA + B-PR | — | 13.16 | 24.15 | 14.14 | 61 | — | 28.11 |
| 5 | B-PR + B-RT | — | 8.46 | 50.36 | 18.17 | 48.91 | — | 31.47 |
| 6 | ACeIN-1 | — | 10.91 | 24.45 | 51.63 | 53.99 | — | 35.25 |
| 7 | ACeIN-2 | — | 10.16 | 26.86 | 40.61 | 52.34 | — | 32.49 |
| 8 | ACeIN-3 | 14.37 | 9.12 | 22.43 | 25.17 | 50.52 | 14.43 | 22.67 |
| 9 | ACeCA | — | 32.34 | 61 | 61 | 61 | — | 53.84 |
| 10 | ACeIN-4 | — | 61 | 61 | 61 | 61 | — | 61 |
| 11 | ACeIN-5 | — | 55 | 61 | 61 | 61 | — | 59.5 |
| 12 | ACeIN-6 | — | 53.12 | 61 | 61 | 61 | — | 59.03 |
| 13 | ACeIN-7 | 14.09 | 9.04 | 14 | 21.3 | 40.81 | 19.08 | 19.72 |
| 14 | ACeIN-8 | 16.66 | 9.86 | 11.89 | 21.19 | 48.82 | 17.39 | 20.97 |
| 15 | ACeIN-9 | — | 34.35 | 61 | 61 | 61 | — | 54.34 |
| 16 | ACeIN-10 | — | 53.87 | 61 | 61 | 61 | — | 59.22 |
| 17 | ACeIN-11 | — | 16.07 | 25.36 | 61 | 51.47 | — | 38.47 |
| 18 | ACeIN-12 | — | 15.94 | 24.72 | 46.73 | 33.02 | — | 30.1 |
| 19 | ACeIN-13 | — | 34.81 | 45.74 | 61 | 61 | — | 50.64 |
| 20 | ACeIN-14 | — | 39.54 | 61 | 61 | 61 | — | 55.63 |
| 21 | ACeIN-15 | — | 19.54 | 29.3 | 56.99 | 61 | — | 41.71 |
| 22 | ACeIN-16 | — | 26.45 | 31.12 | 41.26 | 61 | — | 39.96 |
| 23 | ACeIN-17 | 15.31 | 9.41 | 13.71 | 27.49 | 61 | 13.47 | 23.4 |
| 24 | ACeIN-18 | — | 13.39 | 17 | 25.26 | 43.91 | — | 24.89 |
| 25 | ACeIN-19 | — | 13.08 | 17.29 | 42.85 | 61 | — | 33.55 |
| 26 | ACeIN-20 | — | 15.38 | 20.55 | 61 | 61 | — | 39.48 |
| 27 | ACeIN-21 | — | 47.2 | 52.82 | 61 | 61 | — | 55.51 |
| 28 | ACeIN-22 | — | 46.73 | 59.34 | 61 | 61 | — | 57.02 |
| 29 | ACeIN-23 | — | 10.82 | 16.13 | 24.46 | 61 | — | 28.1 |
| 30 | ACeIN-23 + B-PR | — | 10.45 | 17.14 | 17.62 | 33.89 | — | 19.77 |
| 31 | ACeIN-24 | — | 12.21 | 19.89 | 41.88 | 41.74 | — | 28.93 |
| 32 | ACeIN-25 | — | 8.91 | 14.02 | 14.41 | 46.49 | — | 20.96 |
| 33 | ACeIN-26 | 15.95 | 9.88 | 14.46 | 20.79 | 34.69 | 18.89 | 19.11 |
| 34 | ACeIN-27 | — | 12.55 | 37.7 | 36.48 | 61 | — | 36.93 |
| 35 | ACeIN-28 | 10.69 | 9.4 | 15.99 | 33.39 | 34.83 | 16.57 | 20.15 |
| 36 | ACeIN-29 | 14.02 | 10.68 | 14.87 | 26.12 | 31.39 | 35.95 | 22.17 |
| 37 | ACeIN-30 | 16.69 | 11.33 | 20.64 | 29.01 | 43.2 | 24.25 | 24.19 |
| 38 | ACeIN-31 | 23.25 | 15.02 | 21.67 | 61 | 46.37 | 24.62 | 31.99 |
| 39 | ACeIN-26 + B-PR | 16.1 | 9.05 | 14.73 | 14.8 | 51.26 | 14.05 | 20 |
| 40 | ACeIN-30 + B-PR | 29.95 | 10.38 | 28.49 | 20.33 | 42.46 | 23.09 | 25.78 |
| 41 | ACeIN-28 + B-PR | 11.44 | 9.93 | 33.62 | 21.75 | 46.72 | 13.41 | 22.81 |
| 42 | ACeIN-32 | 16.16 | 10.39 | 15.98 | 29.17 | 51.34 | 17.71 | 23.46 |
| 43 | ACeIN-33 | 16.27 | 10.48 | 15.81 | 22.75 | 50.48 | 16.79 | 22.1 |
| 44 | ACeIN-34 | 15.9 | 10.22 | 14.35 | 22.63 | 51.99 | 27.15 | 23.71 |
| 45 | ACeIN-26 + ACePR | 21.66 | 12.16 | 23.47 | 39.13 | 50.33 | 26.09 | 28.81 |

TABLE 3-continued

| | | | | | | | | |
|---|---|---|---|---|---|---|---|---|
| 46 | ACeIN-26 + F-IN | 14.51 | 12.35 | 15.06 | 13.54 | 43.39 | 15.61 | 19.08 |
| 47 | ACeIN-26 + F-IN + ACePR | 19.69 | 13.08 | 18.45 | 14.91 | 35.13 | 16.09 | 19.56 |

"—" no test was performed. Threshold time of 61 min indicates lack of detectable signal during the experiment Table 4 shows all threshold times generated in this study.

TABLE 4

Table S4. All threshold times generated in this study (5000 target copies) Lack of entry indicates that no experiement was carried out. Threshold time of 61 min indicates lack of detectable signal during the amplification process.

| Primer set | Primer sets name | Experiment | A-UG $T_t$ (min) | B $T_t$ (min) | C $T_t$ (min) | D $T_t$ (min) | F $T_t$ (min) | G $T_t$ (min) | Average $T_t$ (min) |
|---|---|---|---|---|---|---|---|---|---|
| 1 | B-CA | 1.1 | | 13.29 | 48.54 | 13.31 | 52.68 | | |
| | | 1.2 | | 11.9 | 61 | 13.49 | 61 | | |
| | | 1.3 | | 12.47 | | 11.86 | 61 | | |
| | | 1.4 | | 12.41 | | 14.46 | 61 | | |
| | | 1.5 | | 12.45 | | 13.4 | 61 | | |
| | | Average | | 12.5 | 54.77 | 13.3 | 59.34 | | 34.98 |
| | | STD | | 0.5 | 8.81 | 0.93 | 5.89 | | 4.03 |
| 2 | B-PR | 2.1 | | 15.88 | 61 | 15.91 | 55.54 | | |
| | | 2.2 | | 16.35 | 61 | 16.93 | 61 | | |
| | | 2.3 | | 15.83 | 61 | 15.93 | 61 | | |
| | | 2.4 | | 16.65 | 61 | 14.47 | 61 | | |
| | | 2.5 | | 15.65 | 61 | 13.67 | 20.69 | | |
| | | Average | | 16.07 | 61 | 15.38 | 51.85 | | 36.08 |
| | | STD | | 0.41 | 0 | 1.3 | 3.86 | | 1.39 |
| 3 | B-RT | 3.1 | | 9.18 | 61 | 12.6 | 41.78 | | |
| | | 3.2 | | 8.88 | 48.97 | 19.88 | 61 | | |
| | | 3.3 | | 8.9 | 61 | 21.95 | 61 | | |
| | | 3.4 | | 8.64 | 36.63 | 26.25 | 61 | | |
| | | 3.5 | | 8.52 | 56.79 | 18.64 | 57.61 | | |
| | | Average | | 8.82 | 52.88 | 19.86 | 56.48 | | 34.51 |
| | | STD | | 0.25 | 10.33 | 4.99 | 13.59 | | 7.29 |
| 4 | B-CA + B-PR | 4.1 | | 13.4 | 16.58 | 13.77 | 61 | | |
| | | 4.2 | | 12.93 | 31.71 | 14.5 | 61 | | |
| | | Average | | 13.16 | 24.15 | 14.14 | 61 | | 28.11 |
| | | STD | | 0.33 | 10.7 | 0.52 | 0 | | 2.89 |
| 5 | B-PR + B-RT | 5.1 | | 8.46 | 39.71 | 19.39 | 46.48 | | |
| | | 5.2 | | 8.47 | 61 | 16.94 | 51.33 | | |
| | | Average | | 8.46 | 50.36 | 18.17 | 48.91 | | 31.47 |
| | | STD | | 0 | 15.05 | 1.73 | 3.43 | | 5.05 |
| 6 | ACeIN-1 | 6.1 | | 10.98 | 35.57 | 56.75 | 50.4 | | |
| | | 6.2 | | 10.84 | 13.33 | 46.51 | 57.59 | | |
| | | Average | | 10.91 | 24.45 | 51.63 | 53.99 | | 35.25 |
| | | STD | | 0.1 | 15.73 | 7.24 | 5.08 | | 7.04 |
| 7 | ACeIN-2 | 7.1 | | 10.41 | 34.39 | 49.78 | 55.94 | | |
| | | 7.2 | | 9.92 | 19.33 | 31.45 | 48.74 | | |
| | | Average | | 10.16 | 26.86 | 40.61 | 52.34 | | 32.49 |
| | | STD | | 0.34 | 10.65 | 12.96 | 5.09 | | 7.26 |
| 8 | ACeIN-3 | 8.1 | 16.51 | 9.28 | 33.58 | 27.5 | 54.62 | 15.58 | |
| | | 8.2 | 12.22 | 9.67 | 61 | 41.48 | 61 | 13.27 | |
| | | 8.3 | | 9.97 | 13.4 | 12.57 | 61 | | |
| | | 8.4 | | 8.66 | 14.36 | 18.94 | 61 | | |
| | | 8.5 | | 9.26 | 12.97 | 13.88 | 18.83 | | |
| | | 8.6 | | 9.36 | 15.34 | 12.58 | 61 | | |
| | | 8.7 | | 8.3 | 14.29 | 61 | 25.69 | | |
| | | 8.8 | | 8.48 | 14.53 | 13.37 | 61 | | |
| | | Average | 14.37 | 9.12 | 22.43 | 25.17 | 50.52 | 14.43 | 22.67 |
| | | STD | 3.03 | 0.59 | 17.02 | 17.64 | 17.67 | 1.64 | 9.6 |
| 9 | ACeCA | 9.1 | | 32.88 | 61 | 61 | 61 | | |
| | | 9.2 | | 31.81 | 61 | 61 | 61 | | |
| | | Average | | 32.34 | 61 | 61 | 61 | | 53.84 |
| | | STD | | 0.75 | 0 | 0 | 0 | | 0.19 |
| 10 | ACeIN-4 | 10.1 | | 61 | 61 | 61 | 61 | | |
| | | 10.2 | | 61 | 61 | 61 | 61 | | |
| | | Average | | 61 | 61 | 61 | 61 | | 61 |
| | | STD | | 0 | 0 | 0 | 0 | | 0 |
| 11 | ACeIN-5 | 11.1 | | 48.99 | 61 | 61 | 61 | | |
| | | 11.2 | | 61 | 61 | 61 | 61 | | |
| | | Average | | 55 | 61 | 61 | 61 | | 59.5 |
| | | STD | | 8.49 | 0 | 0 | 0 | | 2.12 |
| 12 | ACeIN-6 | 12.1 | | 54.75 | 61 | 61 | 61 | | |
| | | 12.2 | | 51.48 | 61 | 61 | 61 | | |

TABLE 4-continued

Table S4. All threshold times generated in this study (5000 target copies) Lack of entry indicates that no experiement was carried out. Threshold time of 61 min indicates lack of detectable signal during the amplification process.

| Primer set | Primer sets name | Experiment | A-UG $T_t$ (min) | B $T_t$ (min) | C $T_t$ (min) | D $T_t$ (min) | F $T_t$ (min) | G $T_t$ (min) | Average $T_t$ (min) |
|---|---|---|---|---|---|---|---|---|---|
| | | Average | | 53.12 | 61 | 61 | 61 | | 59.03 |
| | | STD | | 2.31 | 0 | 0 | 0 | | 0.58 |
| 13 | ACeIN-7 | 13.1 | 15.81 | 9.4 | 13.48 | 16.81 | 19.31 | 15.55 | |
| | | 13.2 | 12.37 | 9.66 | 15.64 | 32.86 | 41.6 | 22.62 | |
| | | 13.3 | | 8.43 | 11.48 | 17.96 | 61 | | |
| | | 13.4 | | 8.68 | 15.39 | 17.57 | 41.33 | | |
| | | Average | 14.09 | 9.04 | 14 | 21.3 | 40.81 | 19.08 | 19.72 |
| | | STD | 2.44 | 0.5 | 1.68 | 6.69 | 14.75 | 5 | 5.18 |
| 14 | ACeIN-8 | 14.1 | 20.37 | 10.54 | 12.47 | 16.8 | 21.8 | 12.96 | |
| | | 14.2 | 12.95 | 9.94 | 10.71 | 14.68 | 61 | 21.83 | |
| | | 14.3 | | 9.49 | 12.38 | 30.68 | 61 | | |
| | | 14.4 | | 9.46 | 11.99 | 22.59 | 51.48 | | |
| | | Average | 16.66 | 9.86 | 11.89 | 21.19 | 48.82 | 17.39 | 20.97 |
| | | STD | 5.24 | 0.44 | 0.71 | 6.2 | 16.08 | 6.27 | 5.82 |
| 15 | ACeIN-9 | 15.1 | | 35.85 | 61 | 61 | 61 | | |
| | | 15.2 | | 32.85 | 61 | 61 | 61 | | |
| | | Average | | 34.35 | 61 | 61 | 61 | | 54.34 |
| | | STD | | 2.12 | 0 | 0 | 0 | | 0.53 |
| 16 | ACeIN-10 | 16.1 | | 61 | 61 | 61 | 61 | | |
| | | 16.2 | | 46.75 | 61 | 61 | 61 | | |
| | | Average | | 53.87 | 61 | 61 | 61 | | 59.22 |
| | | STD | | 10.08 | 0 | 0 | 0 | | 2.52 |
| 17 | ACeIN-11 | 17.1 | | 16.43 | 26.34 | 61 | 41.93 | | |
| | | 17.2 | | 15.71 | 24.39 | 61 | 61 | | |
| | | Average | | 16.07 | 25.36 | 61 | 51.47 | | 38.47 |
| | | STD | | 0.51 | 1.38 | 0 | 13.48 | | 3.84 |
| 18 | ACeIN-12 | 18.1 | | 16.58 | 24.46 | 61 | 25.39 | | |
| | | 18.2 | | 15.29 | 24.98 | 32.46 | 40.64 | | |
| | | Average | | 15.94 | 24.72 | 46.73 | 33.02 | | 30.1 |
| | | STD | | 0.91 | 0.37 | 20.18 | 10.78 | | 8.06 |
| 19 | ACeIN-13 | 19.1 | | 33.65 | 48.68 | 61 | 61 | | |
| | | 19.2 | | 35.97 | 42.79 | 61 | 61 | | |
| | | Average | | 34.81 | 45.74 | 61 | 61 | | 50.64 |
| | | STD | | 1.64 | 4.16 | 0 | 0 | | 1.45 |
| 20 | ACeIN-14 | 20.1 | | 37.59 | 61 | 61 | 61 | | |
| | | 20.2 | | 41.49 | 61 | 61 | 61 | | |
| | | Average | | 39.54 | 61 | 61 | 61 | | 55.63 |
| | | STD | | 2.76 | 0 | 0 | 0 | | 0.69 |
| 21 | ACeIN-15 | 21.1 | | 20.1 | 24.66 | 52.99 | 61 | | |
| | | 21.2 | | 18.99 | 33.93 | 61 | 61 | | |
| | | Average | | 19.54 | 29.3 | 56.99 | 61 | | 41.71 |
| | | STD | | 0.79 | 6.56 | 5.67 | 0 | | 3.25 |
| 22 | ACeIN-16 | 22.1 | | 25.97 | 30.71 | 30.99 | 61 | | |
| | | 22.2 | | 26.94 | 31.53 | 51.53 | 61 | | |
| | | Average | | 26.45 | 31.12 | 41.26 | 61 | | 39.96 |
| | | STD | | 0.68 | 0.58 | 14.53 | 0 | | 3.95 |
| 23 | ACeIN-17 | 23.1 | 14.7 | 10.23 | 13.84 | 12.83 | 61 | 12.34 | |
| | | 23.2 | 15.92 | 9.58 | 12.47 | 22.66 | 61 | 14.6 | |
| | | 23.3 | | 8.85 | 16.74 | 34.89 | 61 | | |
| | | 23.4 | | 8.99 | 11.8 | 39.57 | 61 | | |
| | | Average | 15.31 | 9.41 | 13.71 | 27.49 | 61 | 13.47 | 23.4 |
| | | STD | 0.87 | 0.55 | 1.9 | 10.48 | 0 | 1.6 | 2.56 |
| 24 | ACeIN-18 | 24.1 | | 14.35 | 14.49 | 30.99 | 26.83 | | |
| | | 24.2 | | 12.43 | 19.51 | 19.52 | 61 | | |
| | | Average | | 13.39 | 17 | 25.26 | 43.91 | | 24.89 |
| | | STD | | 1.36 | 3.55 | 8.12 | 24.16 | | 9.3 |
| 25 | ACeIN-19 | 25.1 | | 13.51 | 15.83 | 24.7 | 61 | | |
| | | 25.2 | | 12.65 | 18.75 | 61 | 61 | | |
| | | Average | | 13.08 | 17.29 | 42.85 | 61 | | 33.55 |
| | | STD | | 0.61 | 2.06 | 25.67 | 0 | | 7.09 |
| 26 | ACeIN-20 | 26.1 | | 16.96 | 20.65 | 61 | 61 | | |
| | | 26.2 | | 13.8 | 20.45 | 61 | 61 | | |
| | | Average | | 15.38 | 20.55 | 61 | 61 | | 39.48 |
| | | STD | | 2.23 | 0.14 | 0 | 0 | | 0.59 |
| 27 | ACeIN-21 | 27.1 | | 49.96 | 61 | 61 | 61 | | |
| | | 27.2 | | 44.45 | 44.64 | 61 | 61 | | |
| | | Average | | 47.2 | 52.82 | 61 | 61 | | 55.51 |
| | | STD | | 3.9 | 11.57 | 0 | 0 | | 3.87 |
| 28 | ACeIN-22 | 28.1 | | 42.81 | 57.68 | 61 | 61 | | |
| | | 28.2 | | 50.66 | 61 | 61 | 61 | | |
| | | Average | | 46.73 | 59.34 | 61 | 61 | | 57.02 |
| | | STD | | 5.55 | 2.35 | 0 | 0 | | 1.98 |

TABLE 4-continued

Table S4. All threshold times generated in this study (5000 target copies) Lack of entry indicates that no experiement was carried out. Threshold time of 61 min indicates lack of detectable signal during the amplification process.

| Primer set | Primer sets name | Experiment | A-UG $T_t$ (min) | B $T_t$ (min) | C $T_t$ (min) | D $T_t$ (min) | F $T_t$ (min) | G $T_t$ (min) | Average $T_t$ (min) |
|---|---|---|---|---|---|---|---|---|---|
| 29 | ACeIN-23 | 29.1 | | 11.69 | 13.99 | 29.43 | 61 | | |
| | | 29.2 | | 9.95 | 18.28 | 19.49 | 61 | | |
| | | Average | | 10.82 | 16.13 | 24.46 | 61 | | 28.1 |
| | | STD | | 1.23 | 3.04 | 7.03 | 0 | | 2.83 |
| 30 | AceIN-23 + B-PR | 30.1 | | 10.93 | 17.5 | 18.4 | 29.55 | | |
| | | 30.2 | | 9.97 | 16.78 | 16.84 | 38.22 | | |
| | | Average | | 10.45 | 17.14 | 17.62 | 33.89 | | 19.77 |
| | | STD | | 0.68 | 0.51 | 1.1 | 6.13 | | 2.1 |
| 31 | ACeIN-24 | 31.1 | | 12.54 | 19.81 | 40.95 | 61 | | |
| | | 31.2 | | 11.88 | 19.97 | 42.81 | 22.47 | | |
| | | Average | | 12.21 | 19.89 | 41.88 | 41.74 | | 28.93 |
| | | STD | | 0.46 | 0.12 | 1.32 | 27.24 | | 7.29 |
| 32 | ACeIN-25 | 32.1 | | 9.16 | 12.53 | 13.92 | 31.99 | | |
| | | 32.2 | | 8.65 | 15.51 | 14.91 | 61 | | |
| | | Average | | 8.91 | 14.02 | 14.41 | 46.49 | | 20.96 |
| | | STD | | 0.36 | 2.11 | 0.7 | 20.51 | | 5.92 |
| 33 | ACeIN-26 | 33.1 | 13.52 | 9.96 | 15.25 | 18.75 | 46.36 | 13.99 | |
| | | 33.2 | 14.25 | 10.99 | 13.32 | 18.36 | 19.79 | 18.72 | |
| | | 33.3 | 17.41 | 9.4 | 15.59 | 24.42 | 33.7 | 33.9 | |
| | | 33.4 | 15.59 | 8.96 | 14.68 | 14.82 | 22.24 | 12.36 | |
| | | 33.5 | 20.4 | 10.22 | 13.6 | 29.6 | 61 | 14.81 | |
| | | 33.6 | 14.55 | 11.22 | 13.96 | 20.81 | 61 | 19.56 | |
| | | 33.7 | | 9.64 | 11.6 | 18.62 | 15.79 | | |
| | | 33.8 | | 8.63 | 17.66 | 20.93 | 17.67 | | |
| | | Average | 15.95 | 9.88 | 14.46 | 20.79 | 34.69 | 18.89 | 19.11 |
| | | STD | 2.56 | 0.91 | 1.8 | 4.49 | 19.07 | 7.86 | 6.12 |
| 34 | ACeIN-27 | 34.1 | | 12.51 | 61 | 35.82 | 61 | | |
| | | 34.2 | | 12.59 | 14.4 | 37.14 | 61 | | |
| | | Average | | 12.55 | 37.7 | 36.48 | 61 | | 36.93 |
| | | STD | | 0.06 | 32.95 | 0.94 | 0 | | 8.49 |
| 35 | ACeIN-28 | 35.1 | 10.43 | 9.28 | 10.79 | 28.57 | 34.4 | 16.21 | |
| | | 35.2 | 10.95 | 9.54 | 17.33 | 30.61 | 13.97 | 16.93 | |
| | | 35.3 | | 9.5 | 18.47 | 13.39 | 61 | | |
| | | 35.4 | | 9.26 | 17.37 | 61 | 29.95 | | |
| | | Average | 10.69 | 9.4 | 15.99 | 33.39 | 34.83 | 16.57 | 20.15 |
| | | STD | 0.37 | 0.13 | 3.04 | 17.27 | 16.91 | 0.51 | 6.37 |
| 36 | ACeIN-29 | 36.1 | 12.72 | 8.96 | 17.67 | 20.4 | 61 | 61 | |
| | | 36.2 | 15.32 | 10.92 | 15.61 | 21.74 | 24.46 | 10.89 | |
| | | 36.3 | | 12.28 | 12.37 | 34.77 | 21.7 | | |
| | | 36.4 | | 10.55 | 13.82 | 27.55 | 18.42 | | |
| | | Average | 14.02 | 10.68 | 14.87 | 26.12 | 31.39 | 35.95 | 22.17 |
| | | STD | 1.84 | 1.18 | 1.98 | 5.67 | 17.23 | 35.43 | 10.56 |
| 37 | ACeIN-30 | 37.1 | 15.42 | 11.9 | 23.39 | 34.57 | 61 | 19.92 | |
| | | 37.2 | 17.97 | 10.76 | 17.88 | 23.46 | 25.41 | 28.58 | |
| | | Average | 16.69 | 11.33 | 20.64 | 29.01 | 43.2 | 24.25 | 24.19 |
| | | STD | 1.8 | 0.81 | 3.89 | 7.85 | 25.17 | 6.12 | 7.61 |
| 38 | ACeIN-31 | 38.1 | 20.93 | 14.54 | 19.5 | 61 | 31.74 | 26.55 | |
| | | 38.2 | 25.56 | 15.5 | 23.84 | 61 | 61 | 22.7 | |
| | | Average | 23.25 | 15.02 | 21.67 | 61 | 46.37 | 24.62 | 31.99 |
| | | STD | 3.27 | 0.68 | 3.06 | 0 | 20.69 | 2.73 | 5.07 |
| 39 | ACeIN-26 + B-PR | 39.1 | 13.68 | 8.45 | 15.84 | 14.68 | 61 | 11.77 | |
| | | 39.2 | 18.52 | 9.65 | 13.61 | 14.93 | 41.52 | 16.33 | |
| | | Average | 16.1 | 9.05 | 14.73 | 14.8 | 51.26 | 14.05 | 20 |
| | | STD | 3.42 | 0.85 | 1.58 | 0.18 | 13.77 | 3.23 | 3.84 |
| 40 | ACeIN-30 + B-PR | 40.1 | 43.96 | 10.27 | 44.57 | 20.69 | 61 | 26.6 | |
| | | 40.2 | 15.94 | 10.5 | 12.4 | 19.97 | 23.93 | 19.58 | |
| | | Average | 29.95 | 10.38 | 28.49 | 20.33 | 42.46 | 23.09 | 25.78 |
| | | STD | 19.81 | 0.16 | 22.75 | 0.51 | 26.22 | 4.96 | 12.4 |
| 41 | ACeIN-28 + B-PR | 41.1 | 12.49 | 10.39 | 54.62 | 18.65 | 61 | 12.93 | |
| | | 41.2 | 10.4 | 9.46 | 12.63 | 24.85 | 32.44 | 13.88 | |
| | | Average | 11.44 | 9.93 | 33.62 | 21.75 | 46.72 | 13.41 | 22.81 |
| | | STDE | 1.48 | 0.66 | 29.7 | 4.39 | 20.19 | 0.68 | 9.51 |
| 42 | ACeIN-32 | 42.1 | 12.8 | 9.94 | 16.35 | 19.75 | 61 | 15.8 | |
| | | 42.2 | 15.38 | 10.68 | 14.89 | 46.73 | 61 | 18.6 | |
| | | 42.3 | 17.86 | 10.51 | 17.86 | 24.72 | 22.38 | 17.96 | |
| | | 42.4 | 18.61 | 10.45 | 14.84 | 25.47 | 61 | 18.47 | |
| | | Average | 16.16 | 10.39 | 15.98 | 29.17 | 51.34 | 17.71 | 23.46 |
| | | STD | 2.63 | 0.32 | 1.43 | 11.98 | 19.31 | 1.3 | 6.16 |
| 43 | ACeIN-33 | 43.1 | 13.52 | 9.86 | 12.26 | 26.99 | 61 | 13.46 | |
| | | 43.2 | 14.84 | 10.5 | 16.32 | 19.78 | 61 | 15.68 | |
| | | 43.3 | 20.48 | 10.96 | 18.93 | 17.44 | 27.23 | 15.37 | |
| | | 43.4 | 16.26 | 10.6 | 15.74 | 26.77 | 52.68 | 22.65 | |

TABLE 4-continued

Table S4. All threshold times generated in this study (5000 target copies) Lack of entry indicates that no experiement was carried out. Threshold time of 61 min indicates lack of detectable signal during the amplification process.

| Primer set | Primer sets name | Experiment | A-UG $T_t$ (min) | B $T_t$ (min) | C $T_t$ (min) | D $T_t$ (min) | F $T_t$ (min) | G $T_t$ (min) | Average $T_t$ (min) |
|---|---|---|---|---|---|---|---|---|---|
|  |  | Average | 16.27 | 10.48 | 15.81 | 22.75 | 50.48 | 16.79 | 22.1 |
|  |  | STD | 3.02 | 0.46 | 2.74 | 4.87 | 15.99 | 4.03 | 5.18 |
| 44 | ACeIN-34 | 44.1 | 15.88 | 10.33 | 13.68 | 16.45 | 24.95 | 19.51 |  |
|  |  | 44.2 | 15.82 | 9.47 | 14.57 | 31.59 | 61 | 14.7 |  |
|  |  | 44.3 | 15.47 | 10.6 | 13.44 | 15.6 | 61 | 61 |  |
|  |  | 44.4 | 16.43 | 10.47 | 15.7 | 26.88 | 61 | 13.4 |  |
|  |  | Average | 15.9 | 10.22 | 14.35 | 22.63 | 51.99 | 27.15 | 23.71 |
|  |  | STD | 0.4 | 0.51 | 1.02 | 7.87 | 18.02 | 22.72 | 8.42 |
| 45 | ACeIN-26 + ACePR | 45.1 | 21.81 | 12.8 | 14.53 | 46.97 | 39.66 | 17.29 |  |
|  |  | 45.2 | 21.52 | 11.53 | 32.41 | 31.29 | 61 | 34.88 |  |
|  |  | Average | 21.66 | 12.16 | 23.47 | 39.13 | 50.33 | 26.09 | 28.81 |
|  |  | STD | 0.2 | 0.9 | 12.64 | 11.08 | 15.09 | 12.44 | 8.72 |
| 46 | ACeIN-26 + F-IN | 46.1 | 14.46 | 12.51 | 14.55 | 14.44 | 61 | 16.97 |  |
|  |  | 46.2 | 14.57 | 12.18 | 15.58 | 12.65 | 25.78 | 14.25 |  |
|  |  | Average | 14.51 | 12.35 | 15.06 | 13.54 | 43.39 | 15.61 | 19.08 |
|  |  | STD | 0.08 | 0.23 | 0.73 | 1.26 | 24.91 | 1.93 | 4.86 |
| 47 | ACeIN-26 + F-IN + ACePR | 47.1 | 22.62 | 14.35 | 19.98 | 15.94 | 44.97 | 13.74 |  |
|  |  | 47.2 | 16.76 | 11.81 | 16.92 | 13.89 | 25.29 | 18.44 |  |
|  |  | Average | 19.69 | 13.08 | 18.45 | 14.91 | 35.13 | 16.09 | 19.56 |
|  |  | STD | 4.15 | 1.79 | 2.16 | 1.45 | 13.92 | 3.32 | 4.47 |

Samples consist of 5000 copies per reaction of HIV-1 templates. The threshold time ($T_t$) is defined as the reaction time that elapses until the florescent signal increases to 10% of maximum fluorescence intensity ($I_{max}$) above the baseline level. For cases where there was no amplification, we designate 61 min as $T_t$.

Examples 3—Testing Different Primer Designs

ACeIN-1 ("Ace" for "all clade", and "IN" for "integrase"), targeted the HIV IN coding region and contained multiple bases at selected sites to broaden detection (FIG. 1). ACeIN-2 and -3 have primers with slightly different landing sites. Tests showed that the mixture of primers allowed amplification with a shorter threshold time than did either alone (FIG. 1).

A new primer set was designed to target the CA coding region (FIG. 1, ACeCA) but found that the set only amplified clade B, and not efficiently. ACeIN3-6 were altered by inserting a polyT sequence between the two different sections of FIP and BIP in various combinations, a modification introduced with the goal of improving primer folding, but these designs performed quite poorly (FIG. 1).

Because the FIP primer appeared to bind the region with most variability among clades, variations that bound to several nearby regions were tried. These were tried with and without the polyT containing BIP and FIP primers in various combinations (FIG. 1, ACeIn7-22). All of the variations of FIP were mixed together (ACeIN-23; Table 1, row 29). The ACeIN-23 primer set was tried as a mixture with the B-PR set to try to capture clade F, yielding a relatively effective primer set (FIG. 1, ACeIN23+B-PR).

In an effort to increase affinity, an additional G/C pair was added F3 and tested with various other IN primers (FIG. 1, ACeIN24-31). Testing showed improvement, with ACeIN-26 showing particularly robust function.

In a second effort to increase primer affinities, locked nucleic acids were added to selected primers binding some of the most conserved bases (FIG. 1, ACeIN 30, 31, 32, 33, and 34). Some improvement was shown over the non-LNA containing bases. However, the ACeIN-26 primer set was as effective as or better than any LNA containing primer sets.

In further tests, the ACeIN-26, 28 and 30 primers were tested combined with the B-PR primer (a slightly modified version of the row 3 primer) but no improvement was seen and efficiency may even have fallen for some subtypes. A primer set was also designed that matched exactly to the problematic subtype F, and this set was mixed with the ACeIN-26 primers. However, no improvement was seen (FIG. 1, mixtures with F-IN set). Mixing the ACeIN-26 primers with both the B-PR (redesigned) and F-specific primers did yield effective primer sets (FIG. 1, ACeIN26+ F-IN and ACeIN26+F-IN+ACePR). However, this was not greatly improved over the ACeIN-26 primer set, so the simpler ACeIN-26 primer set was used in further studies.

Example 4—Performance of the Optimized RT-LAMP Assay

Figure 3:
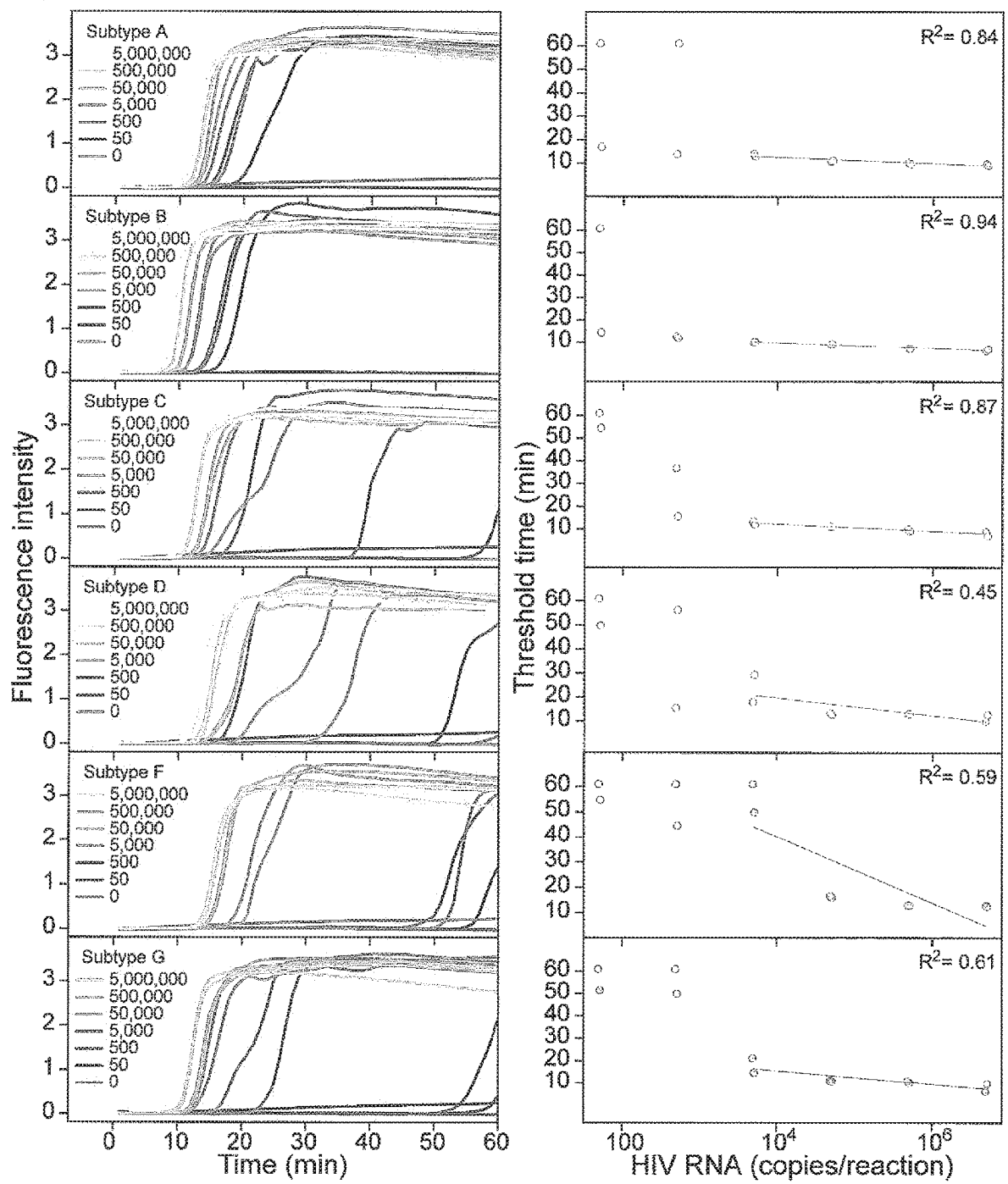
FIG. 3. Performance of the AceIN26 primer set with different starting RNA concentrations. Tests of each subtype are shown as rows. In each lettered panel, the left shows the raw accumulation of fluorescence signal (y-axis) as a function of time (x-axis); the right panel shows the threshold time (y-axis) as a function of log RNA copy number (x-axis) added to the reaction.
Figure 4:
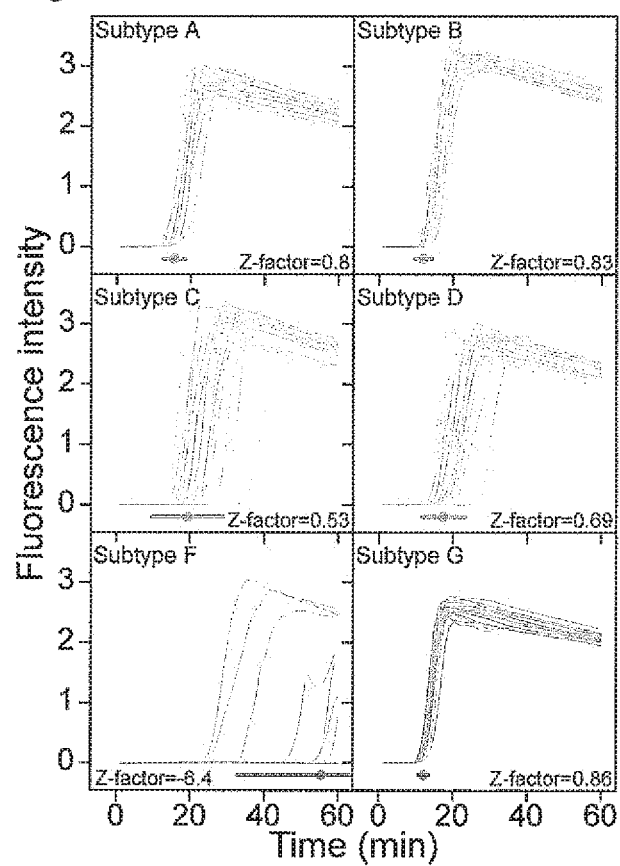
FIG. 4. Examples of time course assays, displaying replicate tests of RT-LAMP primer set ACeIN26 tested over six HIV subtypes. A total of 5000 RNA copies were tested in each reaction. Time is shown on the x-axis, fluorescence intensity on the y-axis. Replicates are distinguished using an arbitrary code. Z-factor values and standard deviations are shown on each panel.

The optimized ACeIN-26 RT-LAMP primer set was tested to determine the minimum concentration of RNA detectable under the reaction conditions studied (FIG. 3). Titrations showed detection after less than 20 min of incubation for 50 copies for subtypes A and B, detection after less than 30 min at 5000 copies for C, D, and G, and detection after less than 20 min of 50,000 copies for F. For clinical implementation the reliability of an assay is critical. This is commonly summarized as a Z-factor, which takes into account both the separation in means between positive and negative samples and the variance in measurement of each. Z-factors for detection of each of the subtypes at 5000 RNA copies per reaction were >0.50 for subtypes A, B, C, D, and G, respectively (FIG. 4). Detection of subtype F at 5000 copies per reaction was sporadic, showing a much lower Z-factor. Tests with z-factor values above 0.5 are judged to be excellent assays, so the ACeIN-26 RT-LAMP primer set is suitable to detect subtype A, B, C, D and G reliably.

Example 5—Subtypes

An RT-LAMP assay optimized to identify multiple HIV subtypes was presented. Infections with subtype B predominate in most parts of the developed world, but elsewhere other clades are more common. Thus nucleic acid-based assay for use in the developing world need to query all subtypes reliably. Previously reported RT-LAMP assays, while effective at detecting subtype B, all showed poor ability to detect at least some of the HIV subtypes (FIG. 1). An initial bioinformatic survey to identify conserved regions all HIV subtypes that could serve as binding sites for RT-LAMP primers was carried out. Primer sets targeting these regions empirically for efficiency were tested. Testing 44 different primer sets revealed that assays containing ACeIN-26 were effective in detecting 5000 copies of RNA from subtypes A, B, C, D, and G within 30 minutes of incubation, and some subtypes were detected even more sensitively. Thus it is proposed that assays based on the ACeIN-26 primer set can be useful assay for quantifying HIV viral load world-wide using RT-LAMP.

Subtypes A, B, C, D, and G were detected efficiently and showed z-factors above 0.5, but subtype F was detected only with higher template amounts. Subtype F is estimated to comprise only 0.59% of all infections globally, so perhaps inefficient detection is still acceptable.

Today, rapid assays are available that can report infection by detecting anti-HIV antibodies in oral samples, allowing simplified assays, but the nucleic-acid based method presented here has additional possible uses. Combining the RT-LAMP assay with simple point of care devices for purifying blood plasma and quantitative analysis of accumulation of fluorescent signals is envisioned. In one implementation of the technology, cell phones could be used to capture and analyze results. Together, these methods will allow assessment of parameters beyond just the presence/absence of infection. Quantitative RT-LAMP assays should allow tracking of responses to medication, detection in neonates (where immunological tests are confounded by presence of maternal antibody), and early detection before seroconversion.

Example 6—Methods—Viral Strains Used in this Study

Viral strains tested included HIV-1 92/UG/029 (Uganda) (subtype A-UG, NIH AIDS Reagent program reagent number 1650), HIV-1 THRO (subtype B, plasmid derived, University of Pennsylvania CFAR) [14], CH269 (subtype C, plasmid derived, University of Pennsylvania CFAR) [14]), UG0242 (subtype D, University of Pennsylvania CFAR), 93BR020 (subtype F, University of Pennsylvania CFAR), HIV-1 G3 (subtype G, NIH AIDS Reagent program reagent number 3187) [15]. Note that the A-UG strain contains subtype A sequences over the target region of ACeIN26, and so was used here to represent subtype A.

Viral stocks were prepared by transfection and infection. Culture supernatants were cleared of cellular debris by centrifugation at 1500 g for 10 min. The supernatant containing virus was then treated with 100 U DNase (Roche) per 450 ul virus for 15 min at 30° C. RNA was isolated using QiaAmp Viral RNA mini kit (Qiagen GmbH, Hilden, Germany). RNA was eluted in 80 µl of the provided elution buffer and stored at −80° C.

Concentration of viral RNA copies was calculated from p24 capsid antigen capture assay results provided by the University of Pennsylvania CFAR or the NIH AIDS-reagent program. In calculating viral RNA copy numbers, it was assumed that all p24 was incorporated in virions, all RNA was recovered completely from stocks, 2 genomes were present per virion, 2000 molecules p24 were present per viral particle, and the molecular weight of HIV-1 p24 was 25.6 kDa.

Example 7—Methods—Assays

RT-LAMP reaction mixtures (15 µL) contained 0.2 µM of primers F3_c, B3_a, and B3_b; 0.8 µM FIP_e, FIP_f, LoopF and LoopB; and 1.6 µM BIP; 7.5 µL OptiGene Isothermal Mastermix IS0-100nd (Optigene, UK), ROX reference dye (0.15µ from a 50× stock), EvaGreen dye (0.4 µL from a 20× stock; Biotium, (Hayward, Calif.); HIV RNA in 4.7 µL; AMV reverse transcriptase (10U/µL) 0.1 µL; and water to 15 µL.

Amplification was measured using the 7500-Fast Real Time PCR system from Applied Biosystems with the following settings: 1 minute at 62° C.; 60 cycles of 30 seconds at 62° C. and 30 seconds at 63° C. Data was collected every minute. Product structure was assessed using dissociation curves which showed denaturation at 83° C. Products from selected amplification reactions were analyzed by agarose gel electrophoresis and showed a ladder of low molecular weight products.

Product synthesis was quantified as the cycle of threshold for 10% amplification. Z-factors were calculated from tests of 24 replicates using the ACeIN26 primer set in assays with viral RNA of each subtype. No detection after 60 min was given a value of 61 min in the Z-factor calculation.

Example 8—Modified ACeIN-26 Primer Set

To improve the amplification efficiency of HIV-1 subtype C the AceIN-BIP primer in ACeIN-26 primer set was modified to better match the HIV subtype C sequence. The modified base site in the modified AceIN-BIP primer (ii) is underlined (R=A, G) below. The mixed primer consists of a 50% R=A and 50% R=G blend. AceIN-BIP primer in ACeIN-26 primer set i)
(SEQ ID NO: 63)
GGAYTATGGAAAACAGATGGCAGCCATGTTCTAATCYTCATCCTG Modified AceIN-BIP Primer (AceIN-BIP-Song)

ii)
(SEQ ID NO: 64)
GGAYTATGGAAAACAGATGGCAGCCATGTTCT<u>R</u>ATCYTCATCCTG.

Figure 5A:
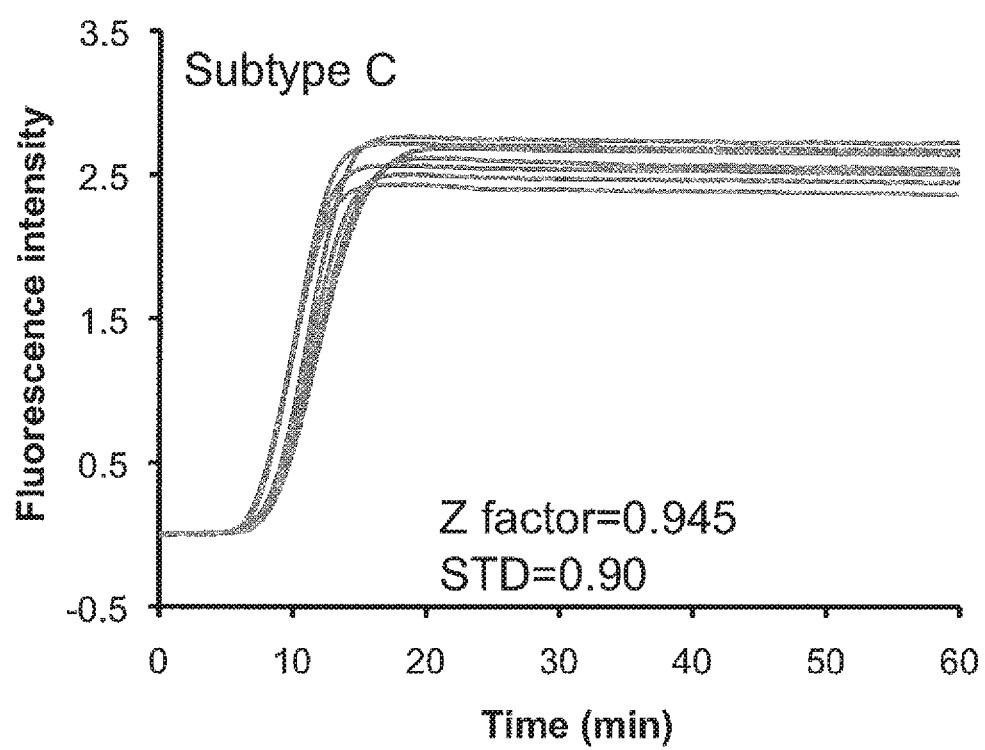
FIGS. 5A and 5B shows emission intensity (arbitrary units) as a function of time when amplifying HIV subtypes C (A, n=7) and B (B, n=7) with modified ACeIN-26 primer set.
Figure 5B:
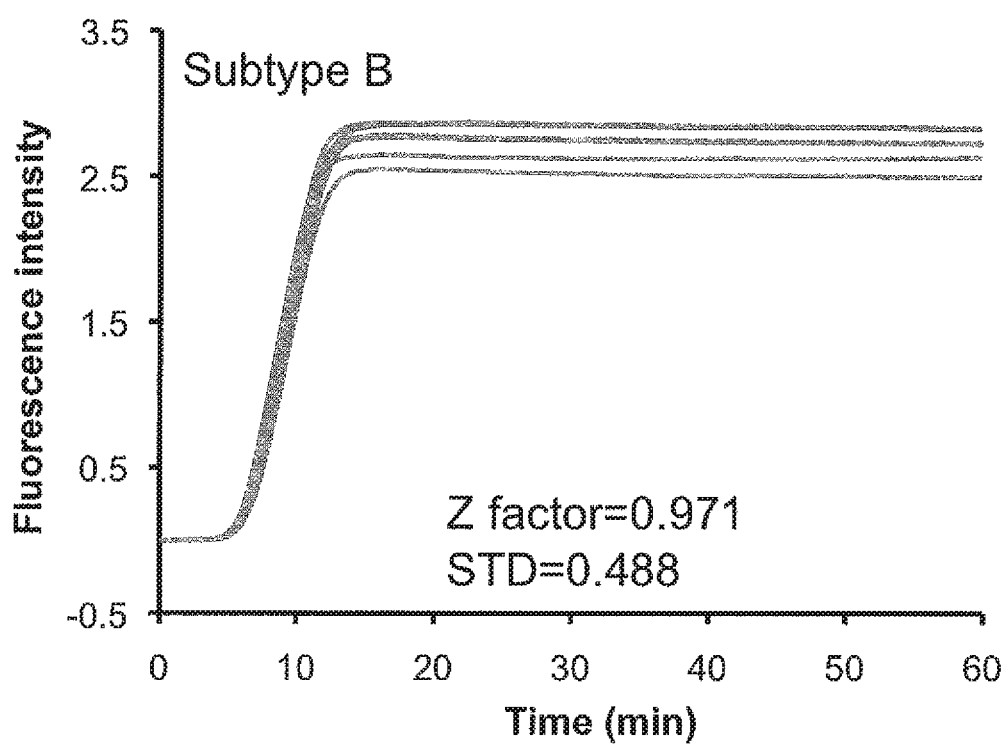

FIG. 5A evaluates the performance of the modified ACeIN-26 primer set with HIV subtypes B and C. Comparison of FIG. 5A with the corresponding panel in FIG. 4 of the main text indicates that the modified ACeIN-26 primer set improved reproducibility and led to a higher Z factor (Z factor=0.945, n=7) (FIG. 5 (A)) than that of ACeIN-26 primer set (Z factor=0.53, n=24) (FIG. 4) when amplifying HIV subtype C. The modified primer set had no adverse effect on the amplification of HIV subtype B (FIG. 5B).

Example 9—HIV Viral Load Test of HIV Subtype C Clinical Sample

The Penn-designed assay for HIV clade C is compatible with clinical samples of HIV patients from Botswana. Since the samples were over three years old, some of the RNA in the samples may have degraded and it was not possible to accurately verify the quantitative aspects of the assay.

Six de-identified plasma samples (Table 5) were collected from HIV patients in Botswana and shipped to the University of Pennsylvania with the approval of the Institutional Review Board.

Table 5 shows information of six plasma samples that were tested.

TABLE 5

| Sample | Collection Date | Viral Load (Copies/mL) | Sample ID |
|---|---|---|---|
| 1 | Feb. 16, 2012 | 3500 | 6053 |
| 2 | Mar. 13, 2012 | 83000 | 6057 |
| 3 | May 21, 2012 | 3500 | 1108 |
| 4 | May 31, 2012 | 4100 | 1113 |
| 5 | Jun. 13, 2012 | 4400 | 1115 |
| 6 | Feb. 28, 2013 | 140000 | 4160 |

The viral loads were determined by quantitative PCR.

The sequences of the HIV RT-LAMP are the same as previously reported (RT-LAMP) primers, ACeIN-26 primer set) with a slight modification in the BIP primer.

Modified BIP:

(SEQ ID NO: 64)
GGAYTATGGAAAACAGATGGCAGCCATGTTCTRATCYTCATCCTG.

Viral RNA was extracted from plasma with a benchtop centrifuge using the QIAamp viral RNA mini kit (QIAGEN, Inc.). Briefly, 140 μL of plasma were mixed with 560 μL AVL buffer containing carrier RNA in a 1.5 mL microcentrifuge tube by pulse-vortexing for 15 seconds followed by incubation at room temperature for 10 min. 560 μL of absolute ethanol were added and mixed by pulse-vortexing for 15 seconds. The lysate were loaded in the QIAamp spin-column mounted on 2 mL collection tubes and centrifuged at 8000 rpm for 1 min. The column was then washed by 500 μL of wash buffers WB1 and WB2. Finally, viral RNA was eluted using 60 μL of AVE buffer. For low viral load samples, like sample IDs 6053, 6057, 1108, 1113 and 1115, 420 μL of plasma was lysed and eluted with 60 μL of AVE buffer to obtain a relatively high target concentration.

The viral RNA was tested on a microfluidic chip. The extracted plasma containing the HIV virus was amplified in a microfluidic chip. Briefly, the chip contains three independent multifunctional, 5.0 mm long, 1.0 mm wide, 3.0 mm deep, and ~15.0 μL in volume amplification reactors. Each of these reactors is equipped with a flowthrough Qiagen silica membrane (QIAamp Viral RNA Mini Kit) at its entry port. The 140 μL of plasma collected with our plasma separator was mixed with 560 μL of lysis buffer (QIAamp Viral RNA Mini Kit, Qiagen, Valencia, Calif.) and inserted into one of the amplification reactors. The nucleic acids bound to the Qiagen silica membrane in the presence of high chaotrophic salts (such as guanidinium chloride) and low pH. Subsequent to the sample introduction, 500 μL of Qiagen wash buffer 1 (AW1), containing chaotropic salt and ethanol, was pipetted into the chip to remove any remaining amplification inhibitors. Then, the silica membrane was washed with 500 μL of wash buffer 2 (AW2) containing 70% ethanol, followed by air drying for 30s. Next, 22 μL of RT-LAMP master mixture, which contains all the reagents necessary for the RT-LAMP, 0.5 ×EvaGreen@fluorescence dye (Biotium, Hayward, Calif.), and 8 units of RNase inhibitor (Life Technologies), was injected into each reaction chamber through the inlet port. Subsequently, the inlet and outlet ports were sealed using transparent tape (Scotch brand cellophane tape, 3M, St. Paul, Minn.) to minimize evaporation during the amplification process. The nucleic acid chip was placed on a portable heater and heated to 63° C. for approximately 60 min. The fluorescence excitation and detection were carried out with a handheld, USB-based, fluorescence microscope (AM4113T-GFBW Dino-Lite Premier, AnMo Electronics, Taipei, Taiwan).

Figure 6:
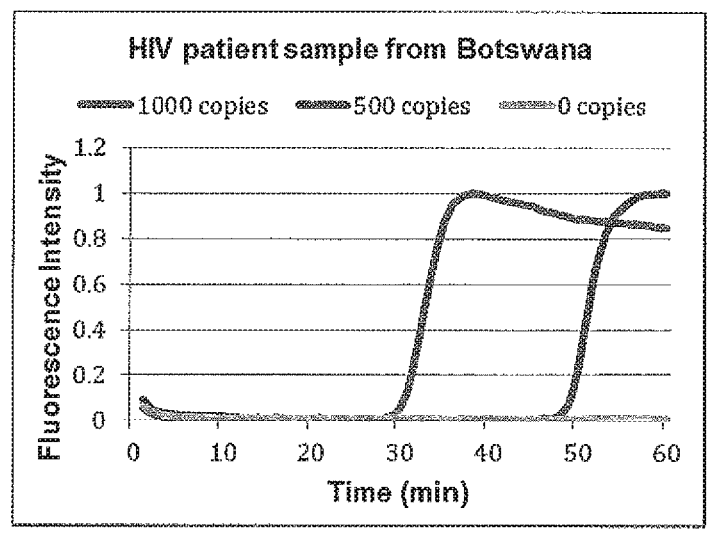
FIG. 6 shows real-time monitoring of RT-LAMP amplification of HIV subtype C sample (sample ID: 4160) nominally containing 1,000, 500, and 0 (negative control) copies per sample on the microfluidic chip. The actual number of RNA copies may be lower due to the age of the sample and possible RNA degradation.

FIG. 6 shows examples of real time RT-LAMP curves of HIV subtype C sample containing 1,000, 500, and 0 (negative control) copies per sample obtained with our microfluidic chip. These samples were prepared by diluting the clinical sample (Sample ID: 4160) with HIV negative plasma. The HIV RNA was extracted by the isolation silica membrane, embedded in our microfluidic chip from sample lysate, and the RNA extracted by the membrane served as a template for RT-LAMP.

Figure 7:
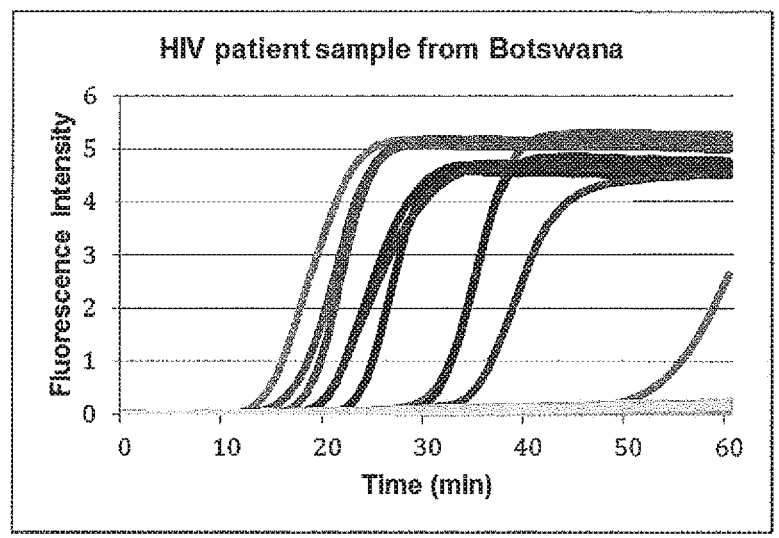
FIG. 7 shows real-time monitoring of RT-LAMP amplification of HIV subtype C sample nominally containing 500 copies per sample on benchtop thermal cycler. 16 replicate tests were run in parallel. The actual number of RNA in the aliquots may have been lower due to the age of the sample and possible RNA degradation.

FIG. 7 depicts real time RT-LAMP curves of 16 replicate purified HIV RNA samples that are extracted from sample 4160. Each sample contains 500 copies that were carried out on the benchtop. Table 2 summarizes the results of the HIV subtype C RT-LAMP assay carried out in our microfluidic chip and in a benchtop thermal cycler. The nominal sensitivity of our chip is 500 copies per reaction.

Table 6 shows HIV subtype C RT-LAMP assay in our microfluidic chip and in a benchtop thermal cycler. The table documents the number of positive results normalized with the number of tests.

TABLE 6

| Samples | Benchtop Testing | On-chip Testing |
|---|---|---|
| 1000 Copies/Reaction | — | 3/3 |
| 500 Copies/Reaction | 10/16 | 3/3 |
| 0 Copies/Reaction (Negative Control) | 0/14 | 3/3 |

Figure 8:
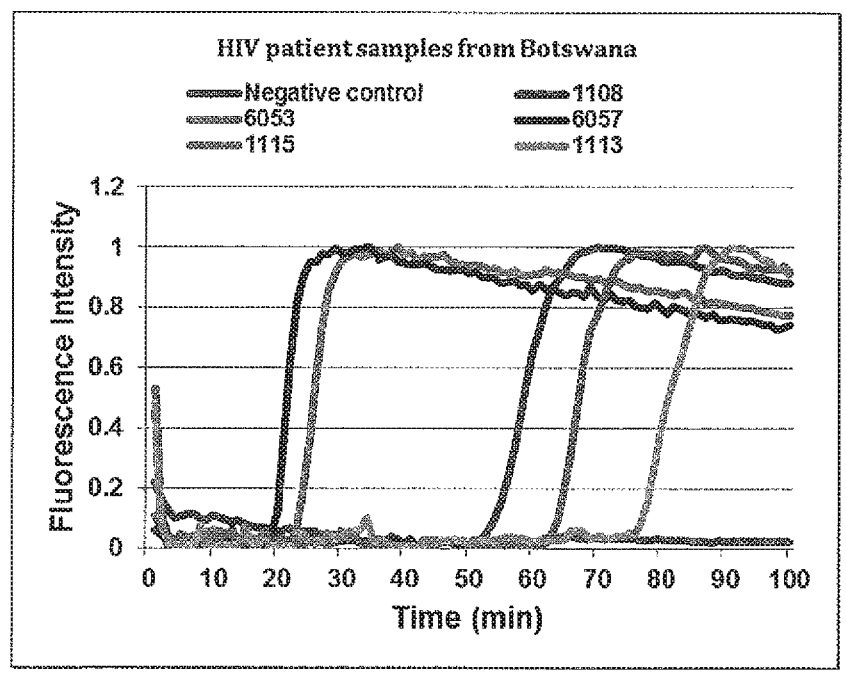
FIG. 8 shows real-time monitoring of RT-LAMP amplification of five HIV subtype C samples (sample ID 6053, 6057, 1108, 1113 and 1115) on the microfluidic chips.

FIG. 8 shows real time RT-LAMP curves of five HIV subtype C samples (samples ID: 6053, 6057, 1108, 1113, and 1115) on our microfluidic chips.

All six samples have been successfully detected on the microfluidic chip with our developed RT-LAMP primers. Less than 500 copies HIV viral RNA can be detected. The experiments indicate that the primers are compatible with clinical samples from Africa.

REFERENCES

1. Murray C J, Ortblad K F, Guinovart C, Lim S S, Wolock T M, et al. (2014) Global, regional, and national incidence and mortality for HIV, tuberculosis, and malaria during 1990-2013: a systematic analysis for the Global Burden of Disease Study 2013. Lancet.
2. Sallis K A, Smit P W, Fiscus S, Ford N, Vitoria M, et al. (2014) Systematic review of the performance ofHIVviralload technologies on plasma samples. PLoS One 9: e85869.
3. Liu C, Mauk M, Gross R, Bushman F D, Edelstein P H, et al. (2013) Membrane-based, sedimentation-assisted plasma separator for point-of-care applications. Anal Chem 85: 10463-10470.
4. Curtis K A, Rudolph D L, Nejad I, Singleton J, Beddoe A, et al. (2012) Isothermal amplification using a chemical heating device for point-of-care detection of HIV-1. PLoS One 7: e31432.

5. Notomi T, Okayama H, Masubuchi H, Yonekawa T, Watanabe K, et al. (2000) Loop-mediated isothermal amplification of DNA. Nucleic Acids Res 28: E63.
6. Curtis K A, Rudolph D L, Owen S M (2008) Rapid detection of HIV-1 by reverse-transcription, loop-mediated isothermal amplification (RT-LAMP). J Virol Methods 151:264-270.
7. Curtis K A, Rudolph D L, Owen S M (2009) Sequence-specific detection method for reverse transcription, loop-mediated isothermal amplification of HIV-1. J Med Virol 81: 966-972.
8. Curtis K A, Niedzwiedz P L, Youngpairoj A S, Rudolph D L, Owen S M (2014) Real-Time Detection of HIV-2 by Reverse Transcription-Loop-Mediated Isothermal Amplification. J Clin Microbial 52: 2674-2676.
9. Kuiken C, Yoon H, Abfalterer W, Gaschen B, Lo C, et al. (2013) Viral genome analysis and knowledge management. Methods Mol Biol 939: 253-261.
10. Manak M, Sina S, Anekella B, Hewlett I, Sanders-Buell E, et al. (2012) Pilot studies for development of an HIV subtype panel for surveillance of global diversity. AIDS Res Hum Retroviruses 28: 594-606.
11. Buonaguro L, Tomesello M L, Buonaguro F M (2007) Human immunodeficiency virus type 1 subtype distribution in the worldwide epidemic: pathogenetic and therapeutic implications. J Virol 81: 10209-10219.
12. Zhang J H, Chung T D, Oldenburg K R (1999) A Simple Statistical Parameter for Use in Evaluation and Validation of High Throughput Screening Assays. J Biomol Screen 4: 67-73.
13. Liu C, Geva E, Mauk M, Qiu X, Abrams W R, et al. (2011) An isothermal amplification reactor with an integrated isolation membrane for point-of-care detection of infectious diseases. Analyst 136: 2069-2076
14. Parrish N F, Gao F, Li H, Giorgi E E, Barbian H J, et al. (2013) Phenotypic properties of transmitted founder HIV-1. Proc Natil Acad Sci US A 110: 6626-6633.
15. Abimiku A G, Stem T L, Zwandor A, Markham P D, Calef C, et al. (1994) Subgroup G HIV type 1 isolates from Nigeria. AIDS Res Hum Retroviruses 10: 1581-1583.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed:

1. A composition, comprising:
   a primer comprising SEQ ID NO: 37;
   a primer comprising SEQ ID NO: 39;
   a primer comprising SEQ ID NO: 41;
   a primer comprising SEQ ID NO: 47;
   a primer comprising SEQ ID NO: 50;
   a primer comprising SEQ ID NO: 63;
   a primer comprising SEQ ID NO: 67; and
   a primer comprising SEQ ID NO: 70.

2. A composition, comprising:
   a primer comprising SEQ ID NO: 37;
   a primer comprising SEQ ID NO: 39;
   a primer comprising SEQ ID NO: 41;
   a primer comprising SEQ ID NO: 47;
   a primer comprising SEQ ID NO: 50;
   a primer comprising SEQ ID NO: 64;
   a primer comprising SEQ ID NO: 67; and
   a primer comprising SEQ ID NO: 70.

3. A method of detecting human immunodeficiency virus (HIV) nucleic acids in a sample from a patient comprising:
   providing a reaction mixture comprising a first primer set or a second primer set for performing a reverse transcription-based loop mediated isothermal amplification assay (RT-LAMP) assay, magnesium, dNTPs, a reaction buffer, a DNA polymerase and a sample to be tested for presence of HIV nucleic acids;
   wherein the first primer set comprises:
   a primer comprising SEQ ID NO: 37;
   a primer comprising SEQ ID NO: 39;
   a primer comprising SEQ ID NO: 41;
   a primer comprising SEQ ID NO: 47;
   a primer comprising SEQ ID NO: 50;
   a primer comprising SEQ ID NO: 63;
   a primer comprising SEQ ID NO: 67; and
   a primer comprising SEQ ID NO: 70; and wherein the second primer set comprises:
   a primer comprising SEQ ID NO: 37;
   a primer comprising SEQ ID NO: 39;
   a primer comprising SEQ ID NO: 41;
   a primer comprising SEQ ID NO: 47;
   a primer comprising SEQ ID NO: 50;
   a primer comprising SEQ ID NO: 64;
   a primer comprising SEQ ID NO: 67; and
   a primer comprising SEQ ID NO: 70;
   incubating the reaction mixture under polymerase reaction conditions so as to produce a reaction product comprising amplified HIV nucleic acids; and detecting the reaction product, wherein the detection has a Z-factor of above 0.5.

4. The method of claim 3, wherein the sample to be tested for presence of HIV nucleic acids comprises one or more subtypes selected from the group consisting of subtype A, B, C, D, and G.

5. The method of claim 3, wherein the detected reaction product is a human immunodeficiency virus nucleic acid of subtype A, B, C, D, or G.

6. The method of claim 4, wherein the detected reaction product is a human immunodeficiency virus nucleic acid of subtype B.

7. The method of claim 3, wherein the detected reaction product comprises HIV integrase coding region of pol gene.

8. The method of claim 3, wherein the sample is a neonate sample comprising maternal antibodies.

9. The method of claim 3, wherein the patient has not undergone seroconversion.

10. A method of monitoring a response to a medication for HIV infection in a subject in need thereof, comprising:
    obtaining a first sample from the subject at a first time point before administering the medication for HIV infection to the subject;
    obtaining a second sample from the subject at a second time point after administering the medication for HIV infection to the subject;
    determining the amount of human immunodeficiency virus (HIV) in the first and second samples, the determining comprising:
    performing a reverse transcription-based loop mediated isothermal amplification (RT-LAMP) on a sample containing HIV using either a first primer set for the first and second samples or a second primer set for the first and second samples, wherein the first primer set comprises:
    a primer comprising SEQ ID NO: 37;
    a primer comprising SEQ ID NO: 39;
    a primer comprising SEQ ID NO: 41;
    a primer comprising SEQ ID NO: 47;
    a primer comprising SEQ ID NO: 50;
    a primer comprising SEQ ID NO: 63;
    a primer comprising SEQ ID NO: 67; and
    a primer comprising SEQ ID NO: 70;
    wherein the second primer set comprises:
    a primer comprising SEQ ID NO: 37;
    a primer comprising SEQ ID NO: 39;
    a primer comprising SEQ ID NO: 41;
    a primer comprising SEQ ID NO: 47;
    a primer comprising SEQ ID NO: 50;
    a primer comprising SEQ ID NO: 64;
    a primer comprising SEQ ID NO: 67; and
    a primer comprising SEQ ID NO: 70; and
    comparing the amount of HIV in the first and second samples,
    wherein a decrease in the amount of HIV from the first sample relative to the second sample indicates a positive response of the subject to the medication treatment of HIV infection.

11. The method of claim 10, wherein the medication is an antiretroviral therapy.

12. The method of claim 10, wherein the sample comprises aqueous humour, vitreous humour, bile, blood, blood serum, breast milk, cerebrospinal fluid, endolymph, perilymph gastric juice, mucus, peritoneal fluid, pleural fluid, saliva, sebum, semen, sweat, tears, vaginal secretion, vomit, or urine.

13. The method of claim 10, wherein the first and/or second sample(s) comprise(s) about 50, about 500, about 1000, about 5000 or about 5500 copies of HIV.

14. The method of claim 3, wherein the sample comprises aqueous humour, vitreous humour, bile, blood, blood serum, breast milk, cerebrospinal fluid, endolymph, perilymph gastric juice, mucus, peritoneal fluid, pleural fluid, saliva, sebum, semen, sweat, tears, vaginal secretion, vomit, or urine.

15. The method of claim 3, wherein the sample comprises about 50, about 500, about 1000, about 5000 or about 5500 copies of HIV.

* * * * *

SEQUENCE LISTING

```
<160> NUMBER OF SEQ ID NOS: 77

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
attatcagaa ggagccacc                                                    19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catcctattt gttcctgaag g                                                 21

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagcttcctc attgatggtt tctttttaac accatgctaa acacagt                     47

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 4
tgttgcacca ggccagataa ttttgtactg gtagttcctg ctatg          45

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttaacattt gcatggctgc ttgat                                25

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagatccaag gggaagtga                                       19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccctttagag actatgtaga cc                                   22

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcctactccc tgacatgc                                        18

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caacaaggtt tctgtcatcc aatttggttc tataaaactc taagagcc       48

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 10
gtccaaaatg cgaacccaga tgtcatcatt tcttctagtg tag                43

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tacctcctgt gaagcttgct c                                        21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttaaaagca ttgggaccag cgg                                      23

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaagataggg gggcaact                                            18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttgacaggt gtaggtccta                                          20

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtttccatc ttcctggcaa attttttctc tattagatac aggagcaga          49

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16 tgatagggggg aattggaggt tttttttccta tagctttatg tccacaga                     48

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttcctatagc tttatgtcca caga                                                 24

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tatcaaagta agacagta                                                        18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aarartaggr ggacagct                                                        18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaaagtaggg ggccagrt                                                        18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaagtaggg ggacagct                                                        18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cactctttgg caacgacc            18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgttgacag gtgtaggycc            20

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtttccatc ttcctggcaa atttttctc tattagayac aggagcaga            49

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgataggrgg aattggaggt tttttccta tagcyttwtk tccacara            48

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgataggrgg aattggaggt tttttgcyt twtktccaca ratttcta            48

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tatdtcttct aatactgtat ca            22

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
atcaaagtaa gacartat                                                18

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29 agttcccttta gataaagact t                                           21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctacataca aatcatccat gt                                           22

<210> SEQ ID NO 31
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtggaagcac attgtactga tatcttttg gaagtatact gcatttacca t            51

<210> SEQ ID NO 32
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggaaaggatc accagcaata ttcctctgga ttttgttttc taaaaggc               48

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggtgtctcat tgtttatact a                                            21

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcatgacaaa aatcttaga                                               19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tatttggaaa ggaccagc                                                   18

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgggtttatt acagrgacag ca                                              22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cctatttgga aaggaccagc                                                 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cctatttgga aaggaccagc                                                 20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tctttgaaay atacatatgr tg                                              22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tctttgaaay atacatatgr tg                                              22

```
<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aacatacata tgrtgyttta cta                                              23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aacatacata tgrtgyttta cta                                              23

<210> SEQ ID NO 43
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cttggtacta cctttatgtc actaaagctc ctctggaaag gtg                        43

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cttggtacta cctttatgtc actattttaa gctcctctgg aaaggtg                    47

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cttggcacta cttttatgtc actaaagctc ctctggaaag gtg                        43

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cttggcacta cttttatgtc actattttaa gctcctctgg aaaggtg                    47
```

```
<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cttggtacta cytttatgtc actaaarcta ctctggaaag gtg                    43

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cttggtacta cytttatgtc actattttaa rctactctgg aaaggtg                47

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cttggtacta cytttatgtc actaaarcta ctctggaaag gtg                    43

<210> SEQ ID NO 50
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cttggcacta cytttatgtc actaaarcty ctctggaaag gtg                    43

<210> SEQ ID NO 51
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cttggcacta cytttatgtc actattttaa rctyctctgg aaaggtg                47

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cttggcacta cytttatgtc actaaarcty ctctggaaag gtg                    43

<210> SEQ ID NO 53
```

```
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctycttggta ctacctttat gtcatactct ggaaaggtga agg            43

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctycttggta ctacctttat gtcattttta ctctggaaag gtg            43

<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cttcttggca ctacttttat gtcatyctct ggaaaggtga agg            43

<210> SEQ ID NO 56
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cttcttggca ctacttttat gtcattttty ctctggaaag gtg            43

<210> SEQ ID NO 57
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggyactacyt ttatgtcact attrtcccta tttggaaagg accagc         46

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggyactacyt ttatgtcact attrtctttt cctatttgga aaggaccagc     50

<210> SEQ ID NO 59
<211> LENGTH: 43
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cttggtacta cctttatgtc actaaaacta ctctggaaag gtg                 43

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cttggtacta cctttatgtc actattttaa actactctgg aaaggtg             47

<210> SEQ ID NO 61
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cttggcacta cttttatgtc actaaagcty ctctggaaag gtg                 43

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cttggcacta cttttatgtc actattttaa gctyctctgg aaaggtg             47

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggaytatgga aaacagatgg cagccatgtt ctaatcytca tcctg               45

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggaytatgga aaacagatgg cagccatgtt ctratcytca tcctg               45

<210> SEQ ID NO 65
<211> LENGTH: 49
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 65
ggaytatgga aaacagatgg cagtttccca tgttctaatc ytcatcctg                49

<210> SEQ ID NO 66
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggaytatgga aaacagatgg cagtttccca tgttctaatc ytcatcctg                49

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tcttgtatta ctactgcccc tt                                             22

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctattgtctt gtattactac tgc                                            23

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctactgcccc ttcacctttc ca                                             22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gtgatgattg tgtggcargt ag                                             22

<210> SEQ ID NO 71
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 71
agtttggaaa ggaccagc                                                      18

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tctttgaaac atgcatatgg ta                                                 22

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aacatacata tggtatttta cta                                                23

<210> SEQ ID NO 74
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cttggtacta cctttatttc actaaagcta ctctggaaag gtg                          43

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ggattatgga aaacagatgg cagccatgtg ttaatcctca tcctg                        45

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cttgtatgac tactgcccct t                                                  21

<210> SEQ ID NO 77
<211> LENGTH: 22
<212> TYPE: DNA
<213> ORGANISM: Artificial Sequence
<220> FEATURE:
```

```
-continued

<223> OTHER INFORMATION: Description of Artificial Sequence: Synthetic
      primer

<400> SEQUENCE: 77
gtgatgattg tgtggcaggt ag                                              22
```